United States Patent
Jay et al.

(10) Patent No.: US 11,752,194 B2
(45) Date of Patent: *Sep. 12, 2023

(54) COMPOSITIONS AND METHODS FOR INHIBITING INTERCELLULAR INTERACTIONS

(71) Applicant: Lubris LLC, Naples, FL (US)

(72) Inventors: Gregory D. Jay, Norfolk, MA (US); Tannin A. Schmidt, Avon, CT (US); Benjamin D. Sullivan, Concord, MA (US)

(73) Assignee: Lubris LLC, Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/196,095

(22) Filed: Mar. 9, 2021

(65) Prior Publication Data

US 2022/0023380 A1    Jan. 27, 2022

Related U.S. Application Data

(62) Division of application No. 16/690,844, filed on Nov. 21, 2019, now Pat. No. 10,960,047, which is a division of application No. 15/039,608, filed as application No. PCT/US2014/067464 on Nov. 25, 2014, now Pat. No. 10,500,250.

(60) Provisional application No. 61/908,959, filed on Nov. 26, 2013.

(51) Int. Cl.
| | |
|---|---|
| *A61K 38/00* | (2006.01) |
| *A61K 38/17* | (2006.01) |
| *A61K 9/00* | (2006.01) |
| *A61K 47/02* | (2006.01) |
| *A01N 1/02* | (2006.01) |

(52) U.S. Cl.
CPC ........ *A61K 38/1709* (2013.01); *A01N 1/0263* (2013.01); *A61K 9/0019* (2013.01); *A61K 47/02* (2013.01)

(58) Field of Classification Search
CPC ... A01N 1/0263; A61K 42/02; A61K 38/1719
See application file for complete search history.

(56) References Cited

U.S. PATENT DOCUMENTS

| | | |
|---|---|---|
| 6,433,142 B1 | 8/2002 | Turner et al. |
| 6,743,774 B1 | 6/2004 | Jay |
| 6,960,562 B2 | 11/2005 | Jay |
| 7,001,881 B1 | 2/2006 | Jay |
| 7,030,223 B2 | 4/2006 | Turner et al. |
| 7,361,738 B2 | 4/2008 | Turner et al. |
| 7,415,381 B2 | 8/2008 | Jay |
| 7,618,941 B2 | 11/2009 | Jay |
| 8,026,346 B2 | 9/2011 | Jay |
| 8,506,944 B2 | 8/2013 | Sullivan et al. |
| 8,551,467 B2 | 10/2013 | Sullivan et al. |
| 8,563,028 B2 | 10/2013 | Sullivan et al. |
| 8,680,057 B2 | 3/2014 | Jay |
| 8,945,604 B2 | 2/2015 | Sullivan et al. |
| 8,980,840 B2 | 3/2015 | Truitt, III et al. |
| 9,107,885 B2 | 8/2015 | Sullivan et al. |
| 9,138,457 B2 | 9/2015 | Sullivan et al. |
| 9,248,161 B2 | 2/2016 | Sullivan et al. |
| 9,393,285 B2 | 7/2016 | Sullivan et al. |
| 9,421,241 B2 | 8/2016 | Sullivan et al. |
| 9,585,936 B2 | 3/2017 | Sullivan et al. |
| 9,730,865 B2 | 8/2017 | Sullivan et al. |
| 9,730,978 B2 | 8/2017 | Sullivan et al. |
| 9,982,027 B2 | 5/2018 | Schmidt |
| 10,125,180 B2 | 11/2018 | Schmidt et al. |
| 10,383,796 B2 | 8/2019 | Truitt et al. |
| 10,500,250 B2 | 12/2019 | Jay et al. |
| 10,500,251 B2 | 12/2019 | Jay et al. |
| 10,723,773 B2 | 7/2020 | Schmidt et al. |

(Continued)

FOREIGN PATENT DOCUMENTS

| | | |
|---|---|---|
| WO | WO-2008/143816 A1 | 11/2008 |
| WO | WO-2011/019963 | 2/2011 |
| WO | WO-2016/123123 A1 | 8/2016 |

OTHER PUBLICATIONS

Al-Sharif A et al., (2015), 'Lubricin/Proteoglycan 4 Binding to CD44 Receptor: A Mechanism of the Suppression of Proinflammatory Cytokine-Induced Synoviocyte Proliferation by Lubricin,' Arthritis Rheumatol, 67(6):1503-13.
Aninwene II Ge et al., (2014), 'Lubricin as a Novel Nanostructured Protein Coating to Reduce Fibroblast Density,' Int J Nanomed, 9(1):3131-5.
Aninwene II Ge et al., (2015), 'Lubricin: A Novel Means to Decrease Bacterial Adhesion and Proliferation,' J Biomed Mater Res A, 103(2):451-62.
Aruffo A, (1996), 'CD44: One Ligand, Two Functions,' J Clin Invest, 98(10):2191-2.
Bakewell SJ et al., (2003), 'Platelet and Osteoclast β3 Integrins are Critical for Bone Metastasis,' Proc Natl Acad Sci USA, 100(24):14205-10.

(Continued)

*Primary Examiner* — Jeanette M Lieb
(74) *Attorney, Agent, or Firm* — Goodwin Procter LLP

(57) ABSTRACT

Disclosed are compositions and methods involving the use of PRG4 protein, also known as lubricin, to mechanically inhibit biological processes involving cell motility and adhesion. The methods and compositions may be used to develop a variety of specific therapies and compositions, often exploited through surgical procedures, where development of the pathology involves one or more of the following modes of action: 1) the passage of cells from one body compartment to another, 2) adherence of macrophages to substrates such as fibrin or exposed extra cellular matrix, 3) binding of platelets to fibrin, or 4) failure of function of the glycocalyx on exposed epithelial cell surfaces, e.g., within the vasculature. In these instances PRG4 glycoprotein adheres to extracellular matrix or cell surfaces and presents a glycol-surface of polysaccharide which blocks the mechanisms of cell motility, extravasation, or intravasation, inhibits sticking of macrophages and platelets, and/or serves as a substitute or mimic of native glycocalyx.

23 Claims, 10 Drawing Sheets

Specification includes a Sequence Listing.

(56) References Cited

U.S. PATENT DOCUMENTS

| | | |
|---|---|---|
| 10,960,047 B2 | 3/2021 | Jay et al. |
| 10,967,048 B2 | 4/2021 | Jay et al. |
| 11,213,566 B2 | 1/2022 | Truitt, III et al. |
| 11,485,764 B2 | 11/2022 | Schmidt et al. |
| 2006/0240037 A1 | 10/2006 | Fey et al. |
| 2007/0111327 A1 | 5/2007 | Jay |
| 2007/0249557 A1 | 10/2007 | Jay |
| 2008/0139458 A1 | 6/2008 | Jay et al. |
| 2008/0287369 A1 | 11/2008 | Jay |
| 2009/0068247 A1 | 3/2009 | Jay |
| 2009/0104148 A1 | 4/2009 | Jay et al. |
| 2009/0155200 A1 | 6/2009 | Jay |
| 2010/0204087 A1 | 8/2010 | Jay |
| 2012/0134925 A1 | 5/2012 | Sullivan et al. |
| 2013/0039865 A1 | 2/2013 | Truitt, III et al. |
| 2013/0116186 A1 | 5/2013 | Jay |
| 2013/0196930 A1 | 8/2013 | Flannery et al. |
| 2013/0315973 A1 | 11/2013 | Jay |
| 2014/0179611 A1 | 6/2014 | Jay |
| 2016/0235809 A1 | 8/2016 | Sullivan et al. |
| 2016/0250286 A1 | 9/2016 | Schmidt |
| 2016/0304572 A1 | 10/2016 | Schmidt et al. |

OTHER PUBLICATIONS

Boyden (1962), "The chemotactic effect of mixtures of antibody and antigen on polymorphonuclear leucocytes," J Exp Med., 115:453-66.

Campo GM et al., (2010), 'Molecular Size Hyaluronan Differently Modulates Toll-Like Receptor-4 LPS-Induced Inflammation in Mouse Chondrocytes,' Biochimie, 92(2):204-15.

Campo GM et al., (2010), 'Small Hyaluronan Oligosaccharides Induce Inflammation by Engaging Both Toll-Like-4 and CD44 Receptors in Human Chondrocytes,' Biochem Pharmacol, 80(4):480-90.

Carlier SG et al., (2003), 'Augmentation of Wall Shear Stress Inhibits Neointimal Hyperplasia After Stent Implantation: Inhibition Through Reduction of Inflammation?,' Circulation, 107(21):2741-6.

Cheng C et al., (2004), 'The Role of Shear Stress in Atherosclerosis: Action through Gene Expression and Inflammation?,' Cell Biochem Biophys, 41(2):279-94.

Coderre et al., (1991) "Increasing sympathetic nerve terminal-dependent plasma extravasation correlates with decreased arthritic joint injury in rats," 40(1):185-189.

Cuff, Carolyn et al., "The adhesion receptor CD44 promotes atherosclerosis by mediating inflammatory cell recruitment and vascular cell activation", The Journal of Clinical Investigation, Oct. 2011, vol. 108, No. 7 (10 pages).

Extended Supplementary European Search Report for European Patent Application No. 14866058.2 dated May 24, 2017 (7 pages).

Fareed J et al., (2015), 'Effect of Recombinant Lubricin on Coagulation Parameters in Human Blood,' FASEB J, 20(1):Suppl 609.8 (Abstract).

Flannery CR et al., (2009), 'Prevention of Cartilage Degeneration in a Rat Model of Osteoarthritis by Intraarticular Treatment with Recombinant Lubricin,' Arthritis Rheum, 60(3):840-7.

Flick MJ et al., (2007), 'Fibrin(ogen) Exacerbates Inflammatory Joint Disease Through a Mechanism Linked to the Integrin αMβ2 Binding Motif,' J Clin Invest, 117(11):3224-35.

Haywood L and Walsh DA, (2001), 'Vasculature of the Normal and Arthritic Synovial Joint,' Histol Histopathol, 16(1):277-84.

Häuselmann I and Borsig L, (2014), 'Altered Tumor-Cell Glycosylation Promotes Metastasis,' Front Oncol, 4(28):1-14.

International Search Report (Form ISA/210) for International Application No. PCT/US2014/067464 dated Mar. 26, 2015 (4 pages).

Jay GD et al., (2001), 'Boundary Lubrication by Lubricin is Mediated by O-Linked β(1-3)Gal—GalNAc Oligosaccharides,' Glycoconj J, 18(10):807-15.

Jay GD et al., (2004), 'Lubricating Ability of Aspirated Synovial Fluid from Emergency Department Patients with Knee Joint Synovitis,' J Rheumatol, 31 (3):557-64.

Jin C et al., (2012), 'Human Synovial Lubricin Expresses Sialyl Lewis x Determinant and has L-selectin Ligand Activity,' J Biol Chem, 287(43):35922-33.

Lauffenburger DA and Horwitz AF, (1996), 'Cell Migration: A Physically Integrated Molecular Process,' Cell, 84(3):359-69.

Lazo-Langner A et al., (2007), 'The Effect of Low-Molecular-Weight Heparin on Cancer Survival. A Systematic Review and Meta-Analysis of Randomized Trials,' J Thromb Haemostas, 5(4)729-37.

Middleton J et al., (2004), 'Endothelial Cell Phenotypes in the Rheumatoid Synovium: Activated, Angiogenic, Apoptotic and Leaky,' Arthritis Res Ther, 6(2):60-72.

Murohara T et al., (1994), 'Polymorphonuclear Leukocyte-Induced Vasocontraction and Endothelial Dysfunction. Role of Selectins,' Artherioscler Thromb, 14(9):1509-19.

Muto J et al., (2009), 'Engagement of CD44 by Hyaluronan Suppresses TLR4 Signaling and the Septic Response to LPS,' Mol Immunol, 47(2-3):449-56.

Palumbo JS et al., (2002), 'Spontaneous Hematogenous and Lymphatic Metastasis, but not Primary Tumor Growth or Angiogenesis, is Diminished in Fibrinogen-Deficient Mice,' Cancer Res, 62(23):6966-72.

Palumbo JS et al., (2005), 'Platelets and Fibrin(ogen) Increase Metastatic Potential by Impeding Natural Killer Cell-Mediated Elimination of Tumor Cells,' Blood, 105(1):178-85.

Raffaghello L and Pistoia V, (2009), 'Editorial: In-and-out Blood Vessels: New Insights into T Cell Reverse Transmigration,' J Leukoc Biol, 86(6):1271-3.

Reitsma S et al., (2007), 'The Endothelial Glycocalyx: Composition, Functions, and Visualization,' Pflugers Arch, 454(3):345-59.

Rhee DK et al., (2005), 'The Secreted Glycoprotein Lubricin Protects Cartilage Surfaces and Inhibits Synovial Cell Overgrowth,' J Clin Invest, 115(3):622-31.

Rodgers KE et al., (2003), 'Reduction of Epidural Fibrosis in Lumbar Surgery with Oxiplex Adhesion Barriers of Carboxymethylcellulose and Polyethylene Oxide,' Spine J, 3(4):277-83.

Schmidt TA et al., (2009), 'Disulfide-Bonded Multimers of Proteoglycan 4 PRG4 are Present in Normal Synovial Fluids,' Biochim Biophys Acta, 1790(5):375-84.

Tzuman YC et al., (2010), 'Peritoneal Adhesion and Angiogenesis in Ovarian Carcinoma are Inversely Regulated by Hyaluronan: The Role of Gonadotropins,' Neoplasia, 12(1):51-60.

Van den Berg BM et al., (2006), 'Atherogenic Region and Diet Diminish Glycocalyx Dimension and Increase Intima-to-Media Ratios at Murine Carotid Artery Bifurcation,' Am J Physiol Heart Circ Physiol, 290(2):H915-20.

Vugmeyster Y et al., (2012), 'Disposition of Human Recombinant Lubricin in Naïve Rats and in a Rat Model of Post-Traumatic Arthritis After Intra-Articular or Intravenous Administration,' AAPS J, 14(1):97-104.

Webb DJ et al., (1999), 'Sildenafil Citrate and Blood-Pressure-Lowering Drugs: Results of Drug Interaction Studies with an Organic Nitrate and a Calcium Antagonist,' Am J Cardiol, 83(5A):21C-28C.

Weinbaum et al., (2007) "The structure and function of the endothelial glycocalyx layer,"Annu Rev Biomed Eng., 9:121-67.

Written Opinion from the International Searching Authority (Form ISA/237) for International Application No. PCT/US2014/067464 dated Mar. 26, 2015 (12 pages).

Wynn et al., (2010), "Mechanisms of fibrosis: therapeutic translation for fibrotic disease," Nature Medicine, 18(7):1028-40.

Yu Q and Stamenkovic I, (1999), 'Localization of Matrix Metalloproteinase 9 to the Cell Surface Provides a Mechanism for CD44-Mediated Tumor Invasion,' Genes Dev, 13(1):35-48.

Zhao et al., (2010), "Effects of a lubricin-containing compound on the results of flexor tendon repair in a canine model in vivo," J. Bone Joint Surg. Am., 92(6):1453-61.

Zhou H, (2010), 'mTOR Signaling in Cancer Cell Motility and Tumor Metastasis,' Crit Rev Eukar Gene Exp, 20(1):1-16.

(56) References Cited

OTHER PUBLICATIONS

European Search Report for European Patent Application No. 22164174 dated Aug. 8, 2022 (5 pages).
Bao, Jia-Peng et al. "Lubricin: a novel potential biotherapeutic approaches for the treatment of osteoarthritis." Molecular biology reports vol. 38,5 (2011): 2879-85.
Nahon, Joya E et al. "Proteoglycan 4 regulates macrophage function without altering atherosclerotic lesion formation in a murine bone marrow-specific deletion model." Atherosclerosis vol. 274 (2018): 120-127.
Nicholas, Emanuele et al., "Effect of Recombinant Lubricin on Human Blood Coagulation Parameters and Platelet Aggregation," FASEB J., Experimental Biology Apr. 1, 2016 Meeting (Abstract).
Sarkar, Anusi et al. "Recombinant human PRG4 (rhPRG4) suppresses breast cancer cell invasion by inhibiting TGFβ-Hyaluronan-CD44 signalling pathway." PloS one vol. 14,7 e0219697. Jul. 30, 2019.

CONTROL

PBS rhPRG4

FIG. 5A
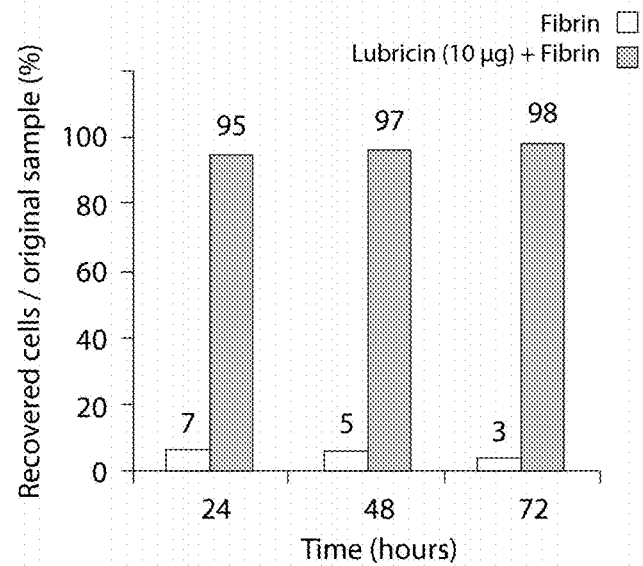
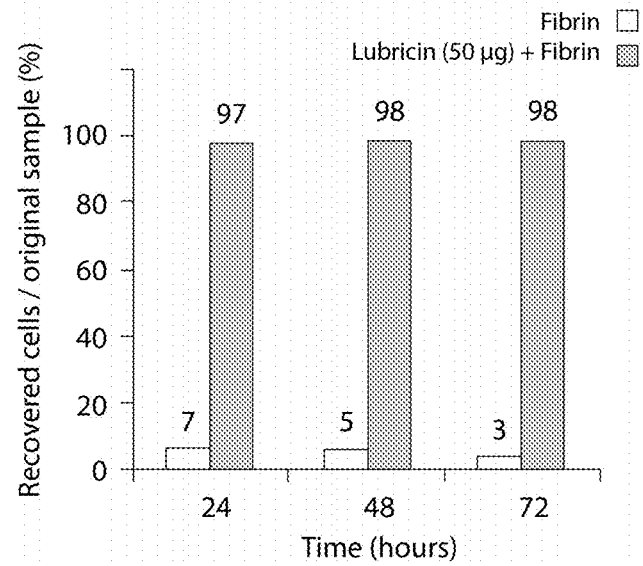
FIG. 5B

FIG. 5C

Inhibition of Macrophage Adhesion*.

| Macrophage number* | Day 0 | 24 hr later | 24 hr F. rate | 48 hr later | 48 hr F. rate | 72 hr later | 72 hr F. rate |
|---|---|---|---|---|---|---|---|
| Fibrin only (0 μg) | 600,000 cells | 40,000 cells | 6.70% | 30,000 cells | 5.00% | 20,000 cells | 3.30% |
| Fibrin + PRG4 (10 μg) | 600,000 cells | 570,000 cells | 95.0% | 580,000 cells | 96.7% | 590,000 cells | 98.3% |
| Fibrin + PRG4 (50 μg) | 600,000 cells | 580,000 cells | 96.7% | 590,000 cells | 98.3% | 590,000 cells | 98.3% |
| Fibrin + PRG4 (100 μg) | 600,000 cells | 560,000 cells | 93.3% | 570,000 cells | 95.0% | 580,000 cells | 96.7% |

*(count for floating cells only)

FIG. 6
SEQ ID NO: 1, LENGTH: 1404, ORGANISM: Homo sapiens, UniProt
Accession No. Q92954:

MAWKTLPIYL LLLLSVFVIQ QVSSQDLSSC AGRCGEGYSR DATCNCDYNC QHYMECCPDF
KRVCTAELSC KGRCFESFER GRECDCDAQC KKYDKCCPDY ESFCAEVHNP TSPPSSKKAP
PPSGASQTIK STTKRSPKPP NKKKTKKVIE SEEITEEHSV SENQESSSSS SSSSSSSTIR
KIKSSKNSAA NRELQKKLKV KDNKKNRTKK KPTPKPPVVD EAGSGLDNGD FKVTTPDTST
TQHNKVSTSP KITTAKPINP RPSLPPNSDT SKETSLTVNK ETTVETKETT TTNKQTSTDG
KEKTTSAKET QSIEKTSAKD LAPTSKVLAK PTPKAETTTK GPALTTPKEP TPTTPKEPAS
TTPKEPTPTT IKSAPTTPKE PAPTTTKSAP TTPKEPAPTT TKEPAPTTPK EPAPTTTKEP
APTTTKSAPT TPKEPAPTTP KKPAPTTPKE PAPTTPKEPT PTTPKEPAPT TKEPAPTTPK
EPAPTAPKKP APTTPKEPAP TTPKEPAPTT TKEPSPTTPK EPAPTTTKSA PTTTKEPAPT
TTKSAPTTPK EPSPTTTKEP APTTPKEPAP TTPKKPAPTT PKEPAPTTPK EPAPTTTKKP
APTTPKEPAP TTPKETAPTT PKKLTPTTPE KLAPTTPEKP APTTPEELAP TTPEEPTPTT
PEEPAPTTPK AAAPNTPKEP APTTPKEPAP TTPKEPAPTT PKETAPTTPK GTAPTTLKEP
APTTPKKPAP KELAPTTTKE PTSTTCDKPA PTTPKGTAPT TPKEPAPTTP KEPAPTTPKG
TAPTTLKEPA PTTPKKPAPK ELAPTTTKGP TSTTSDKPAP TTPKETAPTT PKEPAPTTPK
KPAPTTPETP PPTTSEVSTP TTTKEPTTIH KSPDESTPEL SAEPTPKALE NSPKEPGVPT
TKTPAATKPE MTTTAKDKTT ERDLRTTPET TTAAPKMTKE TATTTEKTTE SKITATTTQV
TSTTTQDTTP FKITTLKTTT LAPKVTTTKK TITTTEIMNK PEETAKPKDR ATNSKATTPK
PQKPTKAPKK PTSTKKPKTM PRVRKPKTTP TPRKMTSTMP ELNPTSRIAE AMLQTTTRPN
QTPNSKLVEV NPKSEDAGGA EGETPHMLLR PHVFMPEVTP DMDYLPRVPN QGIIINPMLS
DETNICNGKP VDGLTTLRNG TLVAFRGHYF WMLSPFSPPS PARRITEVWG IPSPIDTVFT
RCNCEGKTFF FKDSQYWRFT NDIKDAGYPK PIFKGFGGLT GQIVAALSTA KYKNWPESVY
FFKRGGSIQQ YIYKQEPVQK CPGRRPALNY PVYGETTQVR RRRFERAIGP SQTHTIRIQY
SPARLAYQDK GVLHNEVKVS ILWRGLPNVV TSAISLPNIR KPDGYDYYAF SKDQYYNIDV
PSRTARAITT RSGQTLSKVW YNCP

FIG. 7A

SEQ ID NO: 2 LENGTH: 5041, TYPE: DNA, ORGANISM: Homo sapiens, GenBank Accession No. U70136.1:

```
GCGGCCGCGACTATTCGGTACCTGAAAACAACGATGGCATGGAAAACACTTCCCATTTACCT
GTTGTTGCTGCTGTCTGTTTTCGTGATTCAGCAAGTTTCATCTCAAGATTTATCAAGCTGTG
CAGGGAGATGTGGGGAAGGGTATTCTAGAGATGCCACCTGCAACTGTGATTATAACTGTCAA
CACTACATGGAGTGCTGCCCTGATTTCAAGAGAGTCTGCACTGCGGAGCTTTCCTGTAAAGG
CCGCTGCTTTGAGTCCTTCGAGAGAGGGAGGGAGTGTGACTGCGACGCCCAATGTAAGAAGT
ATGACAAGTGCTGTCCCGATTATGAGAGTTTCTGTGCAGAAGTGCATAATCCCACATCACCA
CCATCTTCAAAGAAAGCACCTCCACCTTCAGGAGCATCTCAAACCATCAAATCAACAACCAA
ACGTTCACCCAAACCACCAAACAAGAAGAAGACTAAGAAAGTTATAGAATCAGAGGAAATAA
CAGAAGAACATTCTGTTTCTGAAAATCAAGAGTCCTCCTCCTCCTCCTCCTCTTCCTCTTCT
TCTTCAACAATTTGGAAAATCAAGTCTTCCAAAAATTCAGCTGCTAATAGAGAATTACAGAA
GAAACTCAAAGTAAAAGATAACAAGAAGAACAGAACTAAAAGAAACCTACCCCCAAACCAC
CAGTTGTAGATGAAGCTGGAAGTGGATTGGACAATGGTGACTTCAAGGTCACAACTCCTGAC
ACGTCTACCACCCAACACAATAAAGTCAGCACATCTCCCAAGATCACAACAGCAAAACCAAT
AAATCCCAGACCCAGTCTTCCACCTAATTCTGATACATCTAAAGAGACGTCTTTGACAGTGA
ATAAAGAGACAACAGTTGAAACTAAAGAAACTACTACAACAAATAAACAGACTTCAACTGAT
GGAAAAGAGAAGACTACTTCCGCTAAAGAGACACAAAGTATAGAGAAAACATCTGCTAAAGA
TTTAGCACCCACATCTAAAGTGCTGGCTAAACCTACACCCAAAGCTGAAACTACAACCAAAG
GCCCTGCTCTCACCACTCCCAAGGAGCCCACGCCCACCACTCCCAAGGAGCCTGCATCTACC
ACACCCAAAGAGCCCACACCTACCACCATCAAGTCTGCACCCACCACCCCCAAGGAGCCTGC
ACCCACCACCACCAAGTCTGCACCCACCACTCCCAAGGAGCCTGCACCCACCACCACCAAGG
AGCCTGCACCCACCACTCCCAAGGAGCCTGCACCCACCACCACCAAGGAGCCTGCACCCACC
ACCACCAAGTCTGCACCCACCACTCCCAAGGAGCCTGCACCCACCACCCCCAAGAAGCCTGC
CCCAACTACCCCCAAGGAGCCTGCACCCACCACTCCCAAGGAGCCTACACCCACCACTCCCA
AGGAGCCTGCACCCACCACCAAGGAGCCTGCACCCACCACTCCCAAGAGCCTGCACCCACT
GCCCCCAAGAAGCCTGCCCCAACTACCCCCAAGGAGCCTGCACCCACCACTCCCAAGGAGCC
TGCACCCACCACCACCAAGGAGCCTTCACCCACCACTCCCAAGGAGCCTGCACCCACCACCA
CCAAGTCTGCACCCACCACTACCAAGGAGCCTGCACCCACCACTACCAAGTCTGCACCCACC
ACTCCCAAGGAGCCTTCACCCACCACCACCAAGGAGCCTGCACCCACCACTCCCAAGGAGCC
TGCACCCACCACCCCCAAGAAGCCTGCCCCAACTACCCCCAAGGAGCCTGCACCCACCACTC
```

FIG. 7B

```
CCAAGGAACCTGCACCCACCACCACCAAGAAGCCTGCACCCACCGCTCCCAAGAGCCTGCC
CCAACTACCCCCAAGGAGACTGCACCCACCACCCCCAAGAAGCTCACGCCCACCACCCCGA
GAAGCTCGCACCCACCACCCCTGAGAAGCCCGCACCCACCACCCCTGAGGAGCTCGCACCCA
CCACCCCTGAGGAGCCCACACCCACCACCCCTGAGGAGCCTGCTCCCACCACTCCCAAGGCA
GCGGCTCCCAACACCCCTAAGGAGCCTGCTCCAACTACCCCTAAGGAGCCTGCTCCAACTAC
CCCTAAGGAGCCTGCTCCAACTACCCCTAAGGAGACTGCTCCAACTACCCCTAAAGGGACTG
CTCCAACTACCCTCAAGGAACCTGCACCCACTACTCCCAAGAAGCCTGCCCCAAGGAGCTT
GCACCCACCACCACCAAGGAGCCCACATCCACCACCTCTGACAAGCCCGCTCCAACTACCCC
TAAGGGGACTGCTCCAACTACCCCTAAGGAGCCTGCTCCAACTACCCCTAAGGAGCCTGCTC
CAACTACCCCTAAGGGGACTGCTCCAACTACCCTCAAGGAACCTGCACCCACTACTCCCAAG
AAGCCTGCCCCCAAGGAGCTTGCACCCACCACCACCAAGGGGCCCACATCCACCACCTCTGA
CAAGCCTGCTCCAACTACACCTAAGGAGACTGCTCCAACTACCCCCAAGGAGCCTGCACCCA
CTACCCCCAAGAAGCCTGCTCCAACTACTCCTGAGACACCTCCTCCAACCACTTCAGAGGTC
TCTACTCCAACTACCACCAAGGAGCCTACCACTATCCACAAAAGCCCTGATGAATCAACTCC
TGAGCTTTCTGCAGAACCCACACCAAAAGCTCTTGAAAACAGTCCCAAGGAACCTGGTGTAC
CTACAACTAAGACTCCTGCAGCGACTAAACCTGAAATGACTACAACAGCTAAAGACAAGACA
ACAGAAAGAGACTTACGTACTACACCTGAAACTACAACTGCTGCACCTAAGATGACAAAAGA
GACAGCAACTACAACAGAAAAAACTACCGAATCCAAAATAACAGCTACAACCACACAAGTAA
CATCTACCACAACTCAAGATACCACACCATTCAAAATTACTACTCTTAAAACAACTACTCTT
GCACCCAAAGTAACTACAACAAAAAAGACAATTACTACCACTGAGATTATGAACAAACCTGA
AGAAACAGCTAAACCAAAAGACAGAGCTACTAATTCTAAAGCGACAACTCCTAAACCTCAAA
AGCCAACCAAAGCACCCAAAAAACCCACTTCTACCAAAAAGCCAAAAACAATGCCTAGAGTG
AGAAAACCAAAGACGACACCAACTCCCCGCAAGATGACATCAACAATGCCAGAATTGAACCC
TACCTCAAGAATAGCAGAAGCCATGCTCCAAACCACCACCAGACCTAACCAAACTCCAAACT
CCAAACTAGTTGAAGTAAATCCAAAGAGTGAAGATGCAGGTGGTGCTGAAGGAGAAACACCT
CATATGCTTCTCAGGCCCCATGTGTTCATGCCTGAAGTTACTCCCGACATGGATTACTTACC
GAGAGTACCCAATCAAGGCATTATCATCAATCCCATGCTTTCCGATGAGACCAATATATGCA
ATGGTAAGCCAGTAGATGGACTGACTACTTTGCGCAATGGGACATTAGTTGCATTCCGAGGT
CATTATTTCTGGATGCTAAGTCCATTCAGTCCACCATCTCCAGCTCGCAGAATTACTGAAGT
TTGGGGTATTCCTTCCCCATTGATACTGTTTTACTAGGTGCAACTGTGAAGGAAAACTT
TCTTCTTTAAGGATTCTCAGTACTGGCGTTTTACCAATGATATAAAAGATGCAGGGTACCCC
AAACCAATTTTCAAAGGATTTGGAGGACTAACTGGACAAATAGTGGCAGCGCTTTCAACAGC
```

FIG. 7C

```
TAAATATAAGAACTGGCCTGAATCTGTGTATTTTTTCAAGAGAGGTGGCAGCATTCAGCAGT
ATATTTATAAACAGGAACCTGTACAGAAGTGCCCTGGAAGAAGGCCTGCTCTAAATTATCCA
GTGTATGGAGAAATGACACAGGTTAGGAGACGTCGCTTTGAACGTGCTATAGGACCTTCTCA
AACACACACCATCAGAATTCAATATTCACCTGCCAGACTGGCTTATCAAGACAAAGGTGTCC
TTCATAATGAAGTTAAAGTGAGTATACTGTGGAGAGGACTTCCAAATGTGGTTACCTCAGCT
ATATCACTGCCCAACATCAGAAACCTGACGGCTATGATTACTATGCCTTTTCTAAAGATCA
ATACTATAACATTGATGTGCCTAGTAGAACAGCAAGAGCAATTACTACTCGTTCTGGGCAGA
CCTTATCCAAAGTCTGGTACAACTGTCCTTAGACTGATGAGCAAAGGAGGAGTCAACTAATG
AAGAAATGAATAATAAATTTTGACACTGAAAAACATTTTATTAATAAAGAATATTGACATGA
GTATACCAGTTTATATATAAAAATGTTTTTAAACTTGACAATCATTACACTAAAACAGATTT
GATAATCTTATTCACAGTTGTTATTGTTTACAGACCATTTAATTAATATTTCCTCTGTTTAT
TCCTCCTCTCCCTCCCATTGCATGGCTCACACCTGTAAAAGAAAAAGAATCAAATTGAATA
TATCTTTTAAGAATTCAAAACTAGTGTATTCACTTACCCTAGTTCATTATAAAAATATCTA
GGCATTGTGGATATAAAACTGTTGGGTATTCTACAACTTCAATGGAAATTATTACAAGCAGA
TTAATCCCTCTTTTTGTGACACAAGTACAATCTAAAAGTTATATTGGAAAACATGGAAATAT
TAAAATTTTACACTTTTACTAGCTAAAACATAATCACAAAGCTTTATCGTGTTGTATAAAAA
AATTAACAATATAATGGCAATAGGTAGAGATACAACAAATGAATATAACACTATAACACTTC
ATATTTTCCAAATCTTAATTTGGATTTAAGGAAGAAATCAATAAATATAAAATATAAGCACA
TATTTATTATATATCTAAGGTATACAAATCTGTCTACATGAAGTTTACAGATTGGTAAATAT
CACCTGCTCAACATGTAATTATTTAATAAAACTTTGGAACATTAAAAAAATAAATTGGAGGC
TTAAAAAAAAAAAAAAAAA
```

COMPOSITIONS AND METHODS FOR INHIBITING INTERCELLULAR INTERACTIONS

CROSS-REFERENCE TO RELATED APPLICATIONS

This application is a divisional of U.S. patent application Ser. No. 16/690,844 filed Nov. 21, 2019, which is a divisional of U.S. patent application Ser. No. 15/039,608 filed May 26, 2016, now U.S. Pat. No. 10,500,250, which is a U.S. national stage application filed under 35 U.S.C. § 371 of International Patent Application No. PCT/US2014/067464 filed Nov. 25, 2014, which claims priority to and the benefit of U.S. Provisional Patent Application No. 61/908,959, filed Nov. 26, 2013, the contents of each of which are incorporated by reference herein.

FIELD OF THE INVENTION

This invention relates to compositions and methods involving the use of PRG4 protein, also known as lubricin, to mechanically inhibit biological processes involving cell motility and adhesion. Uses include inhibiting the metastases of cancers; inhibiting formation of intravascular thrombosis which may obstruct blood vessels and result in such events as a stroke, myocardial infarction, pulmonary embolism or the blockage of blood vessels to other parts of the body; inhibiting the formation of fibroses in organs or tissues and at the site of surgical incisions; and improving circulation by protecting exposed endothelium from the development of atherosclerotic plaques, inhibiting the disruption of previously formed plaques, inhibiting restenosis, and reducing shear stress in the vasculature.

BACKGROUND

The proteoglycan 4 gene (PRG4) encodes megakaryocyte stimulating factor (MSF) as well as a highly glycosylated different splice variant and glycoforms of "superficial zone protein" also known as lubricin. Superficial zone protein was first localized at the surface of explant cartilage from the superficial zone and identified in conditioned medium. Lubricin was first isolated from synovial fluid and demonstrated lubricating ability in vitro similar to synovial fluid at a cartilage-glass interface and in a latex-glass interface. It was later identified as a product of synovial fibroblasts, and its lubricating ability was discovered to be dependent on O-linked β (1-3) Gal-GalNAc oligosaccharides within a large mucin like domain of 940 amino acids encoded by exon 6. Lubricin molecules are differentially glycosylated and several naturally occurring splice variants have been reported. They are collectively referred to herein as PRG4. PRG4 has been shown to be present inside the body at the surface of synovium, tendon, articular cartilage such as meniscus, and in the protective film of the eye, among other sites and plays an important role in joint lubrication and synovial homeostasis.

Applicants have determined that beyond its ability to lubricate joints, tendons and cartilage, and the surface of the eye, lubricin may be useful as a therapeutic to treat, prevent, or ameliorate a variety of conditions where the utility of lubricin had not previously been appreciated.

SUMMARY OF THE INVENTION

It has now been discovered that full length lubricin, or PRG4, is present in small concentrations in serum, and can act as a mechanical blockade molecule to physically inhibit cellular binding involved in a number of pathologic biochemical processes. These include metastasis, plaque formation, and thrombus formation. PRG4 capably interrupts platelet and macrophage aggregation when added to a fibrin surface. While the mechanism of its effect has not yet been fully elucidated or deeply examined, the inventors hereof speculate that PRG4 binds to substrates normally bound by vitronectin. As such, PRG4 functions not only as a vitronectin binding inhibitor, but also as a protective coating which binds to exposed ECM and cell surfaces (polymorphonuclear granulocytes) with its heavily glycosylated central domain exposed, and acting as a surface lubricant and masking agent. In these embodiments, it functions as a glycocalyx, inhibiting native cell-cell and cell-matrix interaction.

Vitronectin is an abundant secreted glycoprotein found in serum and extracellular matrix. It binds to cell surfaces, heparin, chondroitin sulfate, collagen, and extracellular matrix (ECM), among other biomolecules, and promotes cell adhesion and motility. It has been speculated to be involved in hemostasis and tumor malignancy. It comprises three domains: an N-terminal somatomedin B domain, a central domain with hemopexin homology, and a C-terminal domain also with hemopexin homology.

The current invention uses applications of the PRG4 protein, appropriately glycosylated, preferably manufactured by expression of the PRG4 gene in a host cell such as Chinese hamster ovary, to mechanically interrupt binding, motility and aggregation of immune, neoplastic or cancer cells. Coatings of PRG4 on physiological surfaces accordingly interrupt a number of pathological processes, and PRG4 can therefore be used in a number of novel ways in therapeutic and prophylactic contexts.

Thus, the invention encompasses methods for mitigating thrombosis and improving circulatory function and health. It also provides ways to inhibit metastasis through boundary layer or film formation which in a load bearing situation is exemplified as boundary lubrication. It can interrupt motility of cancer cells from solid tumors to the vasculature and from the vasculature into the periphery. It also slows or inhibits restenosis of blood vessels after intravascular surgical procedures. The invention also provides methods for reducing or eliminating transplant rejection. The present invention further provides methods to reduce development of fibroses following surgery, e.g., may be used to inhibit formation of scar tissue and fibrotic growth in surgically created holes, grooves, and incisions, in contexts where a surgical incision or passage is intended to remain open post-surgery. Among many examples, it may be used in trabeculoplasty to maintain and improving flow of ocular fluids from the eye.

In one specific aspect, the invention provides compositions and methods to reduce, inhibit or prevent unwanted migration of cells into or out of a compartment of the body through the application of a coating rich in an exogenous PRG4 boundary lubricant onto a surface of a body compartment. Fundamentally, PRG4 mechanically inhibits cell-cell and cell-matrix interaction, thereby providing a method of inhibiting cell-cell adhesion. PRG4 can inhibit in a mammal transient binding interactions between a motile cell and a tissue. Accordingly, in one aspect the invention comprises applying PRG4 to the surface of the motile cell or of the tissue in an amount sufficient to provide a coating which inhibits transient attractive interactions between the cell and the tissue so as to inhibit motility of the cell through, within, or across the surface of the tissue. The cell may be a neoplastic cell, a non-malignant neoplastic cell, a cancer cell, a fibroblast, a macrophage, a neutrophil, eosinophil, basophil, lymphocyte, or a monocyte.

In one embodiment, the invention provides a method for reducing or inhibiting extravasation of cells from the circulatory system of a patient in need thereof by administering by injection directly or indirectly to the vascular system a composition of a physiologically compatible vehicle and PRG4 in an amount sufficient to contact PRG4 with an activated epithelial cell surface of the vasculature to produce a PRG4 film associated with at least a portion of the surface. As a result, a boundary lubricant layer effective at inhibiting or reducing the process of extravasation is provided.

In one embodiment, the cells are leukocytes or neoplastic cells whereas in another embodiment the cells are cancer cells, for example, prostate, breast, lung, or ovarian cancer cells. In another embodiment, the amount of PRG4 administered provides a dose of 0.3 mg/kg to 3.0 mg/kg of PRG4 in the patient. According to the method, administration is by direct or indirect injection into the patient. Injection may involve intravenous injection to provide local or systemic administration. Injection may occur into a body compartment of a patient, for example, the circulatory or vascular system of a patient.

According to one embodiment, the inhibited or reduced extravasation event is one step in the metastasis of a cancer. For example, metastasis to bone, lymph, lung, brain or liver of cancer cells is inhibited or reduced. According to another embodiment, administration of PRG4 occurs in conjunction with surgical, chemotherapeutic, or radiological treatment of a cancer, for example, to inhibit remaining cancer cells from metastasizing to other areas of the body.

In another embodiment, the invention provides a method for reducing or inhibiting intravasation of cells from an extravascular compartment to the circulatory system of a patient in need thereof by administering by injection directly or indirectly to the extravascular compartment a composition comprising a physiologically compatible vehicle and PRG4 in an amount sufficient to contact PRG4 with the cells or cell-surrounding matrix to produce a PRG4 film associated with the surface of the cells or surrounding matrix. As a result, a boundary lubricant layer effective at inhibiting or reducing the native process of cell motility or intravasation is provided.

In one embodiment, the cells are circulating neoplastic cells whereas in another embodiment the cells are cancer cells, for example, prostate, breast, lung, or ovarian cancer cells. In another embodiment, the amount of PRG4 administered provides a dose of 0.3 mg/kg to 3.0 mg/kg of PRG4 in the patient. According to the method, administration is by direct or indirect injection to the patient. Injection may involve intravenous injection to provide local or systemic administration. Injection may occur into an extravascular compartment of a patient, for example, the intraperitoneal space, a tissue, or an organ or at the site of a tumor or at the site of a potential metastasis. In one embodiment, the inhibited or reduced intravasation event is the metastasis of a primary tumor to the circulatory or lymphatic system.

In still another aspect the invention provides methods of maintaining or improving circulatory system function and health by administering by injection directly or indirectly to the circulatory system a maintenance amount of a composition comprising PRG4 and a physiologically compatible vehicle. The amount is sufficient to deliver a concentration sufficient to form a boundary lubricating film of PRG4 at a stressed endothelial surface or plaque within the vascular system.

In one embodiment of this method, the amount of PRG4 administered is sufficient to provide a concentration in the patient of between 0.3 mg/kg and 3.0 mg/kg. In another embodiment, the injection is a systemic intravenous injection or is a localized injection at the site of the stressed endothelial surface or plaque with the vascular system. In yet another embodiment, the PRG4 improves circulatory system function by reducing flow instability within the vascular system.

According to another embodiment, the invention provides methods of inhibiting or reducing vascular thrombus formation by administering by injection directly or indirectly to the circulatory system of a patient a maintenance amount of a composition comprising PRG4 and a physiologically compatible vehicle. The amount is sufficient to deliver a concentration sufficient to form a boundary lubrication film of PRG4 on fibrin and/or platelets present therein.

In one embodiment of this method, the amount of PRG4 administered is sufficient to provide a concentration in the patient of between 0.3 mg/kg and 3.0 mg/kg. In another embodiment, the injection is a systemic intravenous injection or is a localized injection at the site of a thrombosis or at a site at risk of developing a thrombosis. For example, the site may be the site of an injury or tissue damage where clot formation is possible, the site of a developing deep vein thrombosis, or in the lung to prevent or reduce formation of pulmonary embolism.

In yet another embodiment, the invention provides a method of inhibiting vascular restenosis after an intravascular procedure by administering by injection to the circulatory system of a patient systemically or locally at the site of the procedure a composition comprising PRG4 and a physiologically compatible vehicle. PRG4 is provided in an amount sufficient to provide a concentration sufficient to form a boundary lubricating film of PRG4 at an endothelial surface at the site within the vascular system.

In another embodiment, the intravascular procedure is a balloon angioplasty or a stent insertion. In yet another embodiment, the amount of PRG4 administered is sufficient to provide a concentration in the patient of between 0.3 mg/kg and 3.0 mg/kg.

In yet another aspect, the invention provides a method of treating a surgical incision in a patient to maintain patency of the incision and prevent or limit fibrosis at the site of the incision comprising administering PRG4 in a physiologically compatible vehicle to the site of the incision, whereby the lubricin prevents adherence of macrophages to the site of the surgical incision, thereby preventing or limiting fibrosis at the site. According to one embodiment, the PRG4 is administered at a concentration in a vehicle sufficient to provide a coating at a tissue surface, preferably of close packed lubricin molecules noncovalently adhered to the ECM and/or cells of the tissue with their lubricating domains directed upwardly from the tissue surface.

In one embodiment, the surgical incision is in the trabecular meshwork of the eye. Accordingly, the invention provides methods of treating a patient suffering from ocular hypertension or glaucoma to improve the patency and function of a surgically introduced passage through the trabecular framework of the eye. The method comprises applying to surfaces at the surgical site through or near the trabecular meshwork a composition comprising PRG4 in a physiologically compatible vehicle at a concentration sufficient to enhance flow of aqueous humor through the surgically introduced passage. The method reduces the instance of fibrotic clogging and occlusion at the site of the passage in the trabecular meshwork.

In a further embodiment, the invention provides a method of treating, preventing or slowing the progress of fibrosis of an organ or tissue comprising administering, preferably topically, to a patient suffering from or at risk of fibrosis PRG4 in a physiologically compatible vehicle directly or indirectly to the site at risk of fibrosis, whereby the PRG4 inhibits adherence of macrophages at the site, thereby preventing or slowing the progression of fibrosis.

In yet another embodiment, the invention provides a method of inhibiting transplant rejection comprising administering to the exterior surface of a transplanted organ or tissue, and/or to the surface of a body compartment containing a transplanted organ or tissue, and/or to the vasculature of a patient having a transplanted organ or tissue a composition comprising a physiologically compatible vehicle and PRG4 at a concentration sufficient to contact a cell surface with PRG4 to produce a PRG4 film associated with the surface thereby to present a boundary lubricant layer effective at inhibiting normal cell-cell interaction and to inhibit rejection of said transplanted organ or tissue. According to the invention, the transplanted organ or tissue may be but is not limited to liver, kidney, heart, lung, eye tissue, tendon, or skin.

In any of the embodiments of this invention the patient may be a human patient.

In a further embodiment, the invention is directed to equipment for processing blood, specifically, the portions or compartments of the equipment that contact blood, is coated with lubricin. The equipment may include dialysis equipment, or a heart-lung machine or equipment for processing blood transfusions and blood samples. In yet another embodiment, containers for holding and processing blood samples, such as vials, IV bags, or other containers are coated with PRG4.

BRIEF DESCRIPTION OF THE DRAWINGS

FIG. 3B), and blood treated with recombinant human PRG4 (rhPRG4; FIG. 3C). While a clot formed in untreated blood and blood treated with PBS, blood treated with rhPRG4 resists clotting and flows freely in the bottom of the Hula Cup.

FIG. 4A) and pathological plasma (path plasma; FIG. 4B) pooled from liver disease patients as measured by optical density over time. In FIG. 4A, the plotted data curve lines are top to bottom 0 mg/mL lubricin (x), 50 mg/mL lubricin (▲), 100 mg/mL lubricin (■) and 200 mg/mL (♦) lubricin. In FIG. 4B, the plotted data curve lines are top to bottom 50 mg/mL lubricin (▲), 100 mg/mL lubricin (■), 0 mg/mL lubricin (x), and 200 mg/mL (♦) lubricin.

FIGS. 5A-B are bar graphs presenting data demonstrating the ability of PRG4 to interrupt macrophage adhesion to a fibrin surface under conditions similar to those described for the experiment in FIGS. 2A-B. Essentially no macrophages are able to bind to the fibrin surface when PRG4 is added to the plate, with cell recoveries near 100% at 24, 48 and 72 hours following exposure. This supports the hypothesis that PRG4 has a long-lasting and potent ability to interrupt interactions of cells and matrix. FIG. 5C provides cell count data recording the percentages of free macrophages recovered from a fibrin surface with and without PRG4. Because the effect is mechanical in nature, PRG4 protects the surface equally well against adhesion of a variety of other circulating cell types, including cancer cells.

FIG. 6 is the amino acid sequence of full length (non-truncated) human PRG4 (SEQ ID NO:1; 1404 residues). Residues 1-24 (shown in bold) represent the signal sequence and residues 25-1404 represent the mature sequence of human PRG4. The glycoprotein does not require the lead sequence in its active form.

FIGS. 7A-C provide the nucleic acid sequence for the PRG4 gene (SEQ ID NO:2) encoding the full length 1404 AA human PRG4 protein. The sequence begins in FIG. 7A and extends through FIG. 7B, ending in FIG. 7C.

DETAILED DESCRIPTION OF THE INVENTION

Figure 1:
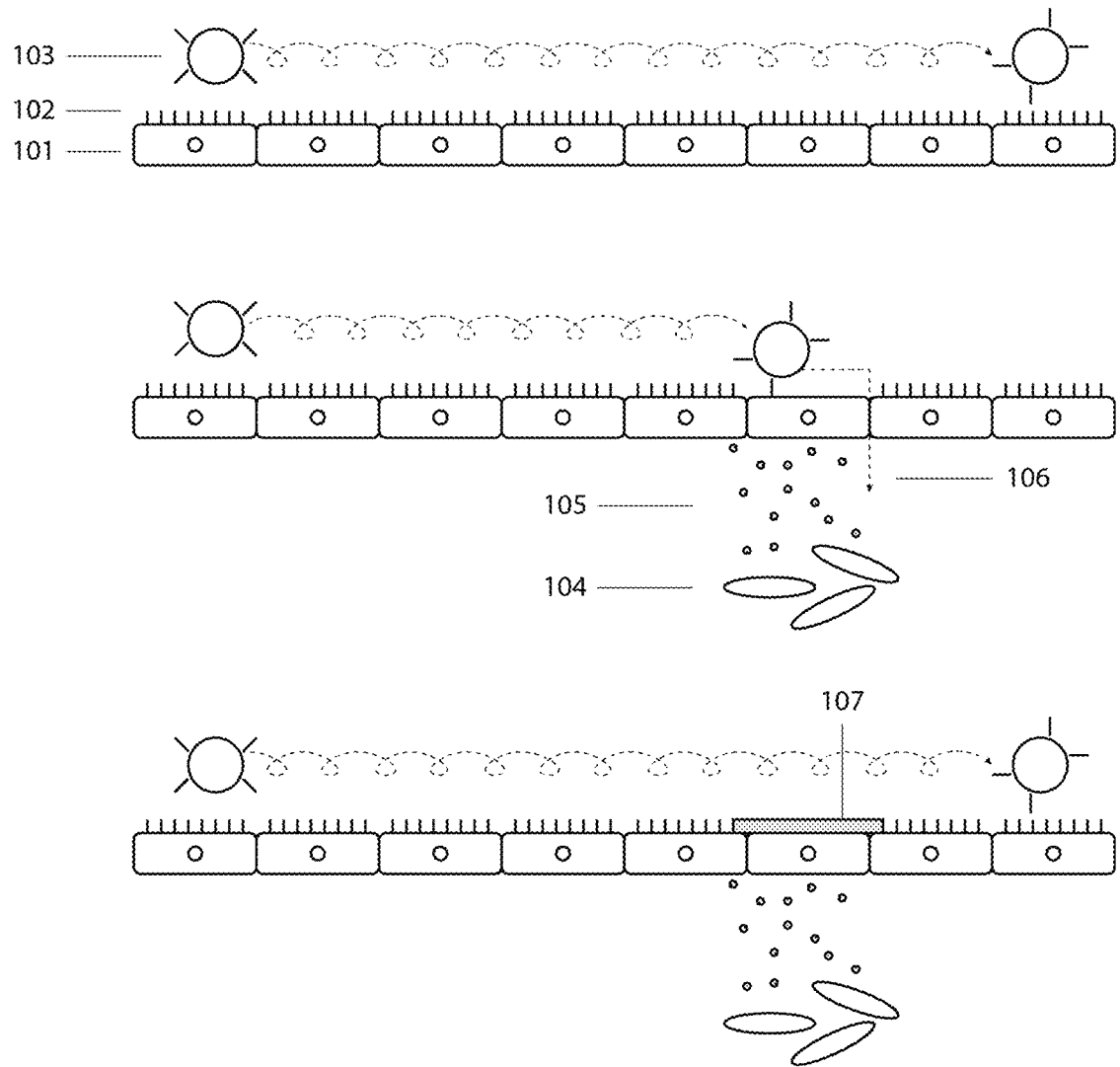
FIG. 1 is a cartoon depicting the interaction between endothelial cells in the vascular endothelial bed 101, the approximately 500 nm in depth, highly charged glycocalyx 102, and immune cells 103 traversing along the endothelium, sampling the surface as it rolls. When peripheral inflammation is present 104, whether acute, chronic or auto-immune, a cytokine gradient 105 signals certain endothelial cells to down regulate or cleave the protective glycocalyx 102, exposing surface receptors and hydrophobic binding sites, allowing immune cells to adhere, then extravasate, migrating as shown by arrow 106 down the gradient. The presence of a suitable, spontaneously adherent boundary lubricant 107, e.g., PRG4 or lubricin, provides an adhesive, i.e., anti-adhesive surface of exposed glycosylation and the immune cell is no longer able to adhere or activate. This thereby interrupts the flow of cells out of the vasculature (extravasation). The same fundamental mechanism applies when PRG4 is used in an extravascular compartment which has developed a solid tumor, but the PRG4 acts instead to inhibit shed tumor cells from the cancer from migrating out of the compartment, or across a vascular or tissue interface. In essence, lubricin acts as a mechanical barrier, preventing cell attachment and subsequent motility.

The function of PRG4 heretofore has been almost entirely associated with prevention of wear between articulating joints and lubrication of interfacing tissues such as in the between the cornea and conjunctiva of the eye. Use of a systemic boundary lubricant such as PRG4 protein for the purposes and uses described in the present invention to applicants' knowledge have not been previously suggested, possibly because the major component of the vascular endothelial glycocalyx (syndecans, glypicans, perlecans, versicans, decorin, biglycan, and mimecan, along with GAGs such as heparan sulfate, chondroitin sulfate, dermatan sulfate, and hyaluronic acid reported in the literature (e.g., Weinbaum S, Tarbell J M, Damiano E R, Annu. Rev. Biomed. Eng. 2007. 9:121-67 & Pflugers Arch—Eur J Physiol (2007) 454:345-359)) do not include PRG4.

The functional importance of PRG4 in joint maintenance has been shown by mutations that cause the camptodactylyarthropathy-coxa vara-pericarditis (CACP) disease syndrome in humans. CACP is manifest by camptodactyly, noninflammatory arthropathy, and hypertrophic synovitis, with coxa vara deformity, pericarditis, and pleural effusion. Also, in PRG4-null mice, cartilage deterioration and subsequent joint failure were observed. Therefore, PRG4 expression is a necessary component of healthy synovial joints.

For the invention claimed herein, reduction in metastases is achieved by supplementation of local (within a specific body compartment) or systemic (within the vasculature) boundary lubrication using PRG4. PRG4 binds to endothelial surfaces and may be used as a device or agent in vivo to inhibit cell motility mechanisms, and prevent the unwanted migration of cells, e.g., across surfaces, through tissues, or between physiological compartments.

Physicochemical modes of lubrication broadly have been classified as "fluid film" or boundary. In biological systems, the operative lubrication modes depend on the normal and tangential forces on the articulating tissues, on the relative rate of tangential motion between these surfaces, and on the time history of both loading and motion. The friction coefficient, $\mu$, provides a quantitative measure, and is defined as the ratio of tangential friction force to the normal force. One type of fluid-mediated lubrication mode is hydrostatic. At the onset of loading and typically for a prolonged duration, interstitial fluid becomes pressurized, due to the biphasic nature of tissue; fluid may also be forced into the asperities between articular surfaces through a weeping mechanism. Pressurized interstitial fluid and trapped lubricant pools may therefore contribute significantly to the bearing of normal load with little resistance to shear force, facilitating a low $\mu$. Also, at the onset of loading and/or motion, squeeze film, hydrodynamic, and elasto-hydrodynamic types of fluid film lubrication occur, with pressurization, motion, and deformation acting to drive viscous lubricant from and/or through the gap between two surfaces in relative motion.

In some instances, the relevant extent to which fluid pressure/film versus boundary lubrication occurs depends on a number of factors. When lubricant film can flow between the conforming sliding surfaces, which can deform elastically, elasto-hydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. In certain instances, the boundary mode of lubrication is therefore indicated by a friction coefficient during steady sliding being invariant with factors that influence formation of a fluid film, such as relative sliding velocity and axial load. For certain tissues in the body, such as articular cartilage, it has been concluded that boundary lubrication occurs, and is complemented by fluid pressurization and other mechanisms. In traditional boundary lubrication theory, increasing loading time and dissipation of hydrostatic pressure allows lubricant-coated surfaces to bear an increasingly higher portion of the load relative to pressurized fluid, and consequently, this mode can become increasingly dominant.

The inventors hereof have recognized that the velocity profile of blood and lymph flowing through the vasculature approximates the no-slip condition used in fluid mechanics to describe a radially dependent reduction in velocity and concurrent increase in blood pressure near the walls of a vessel to create the ideal conditions for boundary lubrication. It is also recognized that surface bound glycoproteins are largely responsible for the transmission of shear stress to the endothelial cells, and that mechanotransduction of that shear is necessary for proper regulation of cell morphology, nitric oxide (NO) production, cytoskeletal reorganization and hyaluronan content (Pflugers Arch—Eur J Physiol (2007) 454:345-359). In particular, areas of low shear, unstable and oscillatory flow are prone to atherosclerosis, impaired NO production and an increase in hyaluronidase. Similarly, improvement in shear transmission is associated with an increase in glycocalyx thickness and hyaluronan content. Laminar flows within normal tissue result in an approximately 400 nm glycocalyx thickness, while regions exposed to disturbed flow exhibited thinner coatings of less than 100 nanometers (van den Berg B M, et al. (2006) Am J Physiol Heart Circ Physiol 290:H915-H920).

Accordingly, the present invention, among other aspects, contemplates the application of recombinant, exogenous surface binding lubricant PRG4, typically by introduction into the vasculature, to: 1) provide increased boundary lubrication (and steric masking of underlying receptors, integrins and selectins, etc.) between cells and cell interfaces to prevent or substantially reduce extravasation of cells between compartments (e.g., rolling, adhesion, transmigration/diapedesis); 2) bind to endogenous exposed endothelial cells to improve the transmission of shear to the underlying cells (e.g., improved mechanotransduction, improved nitric oxide production, improved production of endogenous glycocalyx); 3) extend the glycocalyx further into the lumen to smooth out the flow, reduce oscillations, instabilities, and improve laminar flow, and 4) replace, mask or compete with endogenous aberrant PRG4 so as to prevent binding to L-selectin on polymorphonuclear granulocytes.

As disclosed herein, PRG4 may provide boundary lubrication along the walls of the vasculature. In some embodiments, it protects peripheral tissues from extravasation of cells such as cancer cells, helps to transmit shear stress to underlying endothelium, and reduces surface roughness to reduce fluid instability.

The methods and compositions may be used to develop a variety of specific therapies and compositions, often exploited through surgical procedures, where development of the pathology involves one or more of the following modes of action: 1) the passage of cells from one body compartment to another, 2) adherence of macrophages to exposed extracellular matrix or fibrin 3) binding of platelets to fibrin, or 4) failure of function of the glycocalyx on exposed epithelial cell surfaces, e.g., within the vasculature. In these instances PRG4 protein adheres to extracellular matrix or cell surfaces and presents a glycosylated surface of short polysaccharide chains which blocks the mechanisms of cell motility, extravasation, or intravasation, inhibits sticking of platelets, and/or serves as a substitute or mimic of native glycocalyx. As examples, PRG4 may be used to inhibit metastases of cancers, thereby preventing unwanted migration of cancer cells into or out of a physiological compartment of the body. As another example, PRG4 may be exploited to mechanically interrupt binding, motility and aggregation of immune cells, inhibit formation of intravascular thrombosis. Most generally, the invention achieves these effects through the direct or indirect application to tissue surfaces of exogenous PRG4 protein, which behaves in vivo as a boundary lubricant.

For the invention claimed herein, reduction in metastases is achieved by supplementation of local (within a specific body compartment) or systemic (within the vasculature) boundary lubrication using PRG4. PRG4 binds to endothelial surfaces and may be used as a device or agent in vivo to inhibit cell motility mechanisms, and prevent the unwanted migration of cells, e.g., between physiological compartments.

As used herein, "body compartment" or "physiological compartment" refers to any locality that is physically separated by a tissue from others and houses a tissue or system of interest. In the case of a solid tumor, the compartment is the tissue immediately surrounding the tumor boundary. In the case of a surgically applied incision, e.g., during minimally invasive glaucoma surgery, it would comprise the void left by the incision. In the case of closed-angle glaucoma surgery, the compartment is defined as the anterior chamber. In the case of preventing transplant rejection, the compartment would be the tissue surrounding the transplant. In the case of inhibiting restenosis, the compartment would be the inside of the vessels that receives the stent or other surgical insult.

In order for cancer cells to successfully colonize a metastatic site, they must detach from the primary tumor using extracellular matrix-degrading proteases, intravasate and survive in the circulation, evade the immune response, and extravasate the vasculature to invade the target tissue parenchyma, where metastatic foci are established. The methods of invention can be used to prevent or reduce the incidence of intravasation, i.e., movement of cells from the tissues into the blood or lymph. With respect to these cells, the methods of the invention can also be used to prevent or reduce the incidence of extravasation, i.e., movement of cells from the blood into the tissues and organs of the body. In particular, the methods of the invention can be used to prevent metastases to the lymph, lungs, liver, brain, and/or bones of cancer and neoplastic cells. These are the most common body tissues for metastasis by primary tumors, although the methods of the invention can be used to prevent or reduce metastasis to other organs and tissues.

The Active PRG4 Moiety

Lubricin is a lubricating polypeptide, which in humans is expressed from the megakaryocyte stimulating factor (MSF) gene, also known as PGR4 (see NCBI Accession Number AK131434-U70136). Lubricin is a ubiquitous, endogenous glycoprotein that coats the articulating surfaces of the body [Jay G D 2004]. Lubricin is highly surface active molecule (e.g., holds onto water), that acts primarily as a potent cytoprotective, anti-adhesive and boundary lubricant. It is characterized by a long, central mucin-like domain located between terminal protein domains that allow the molecule to adhere and protect tissue surfaces. Its natural form, in all mammals investigated, contains multiple repeats of an amino acid sequence which is at least 50% identical to KEPAPTT. Natural lubricin typically comprises multiple redundant forms of this repeat, but typically includes proline and threonine residues, with at least one threonine being glycosylated in most repeats. The threonine anchored O-linked sugar side chains are critical for lubricin's boundary lubricating function. The side chain moiety typically is a β(1-3)Gal-GalNAc moiety, with the β(1-3)Gal-GalNAc typically capped with sialic acid or N-acetylneuraminic acid [Jay G D 2001]. The polypeptide also contains N-linked oligosaccharides. The gene encoding naturally-occurring full length lubricin contains 12 exons, and the naturally-occurring MSF gene product contains 1,404 amino acids with multiple polypeptide sequence homologies to vitronectin including hemopexin-like and somatomedin-like regions. Centrally-located exon 6 contains 940 residues. Exon 6 encodes the repeat rich, O-glycosylated mucin domain.

The amino acid sequence of the protein backbone of a lubricating polypeptide may differ depending on alternative splicing of exons of the human MSF gene. Because lubricin serves a fundamentally mechanical function, its fine tertiary structure is less critical than proteins such as cytokines or antibodies which depend on subtle stereochemistry which governs binding to receptors. This robustness against heterogeneity was exemplified when researchers created a recombinant form of lubricin missing 474 amino acids from the central mucin domain, yet still achieved reasonable, although muted, lubrication [Flannery C R 2009]. PRG4 has been shown to exist not only as a monomer but also as a dimer and multimer disulfide-bonded through the conserved cysteine-rich domains at both N- and C-termini [Schmidt T A 2009]. Lμbris, LLC has developed a full-length recombinant form of human lubricin. The molecule is expressed using the Selexis Chinese hamster ovary cell line (CHO-M), with a final apparent molecular weight of 450-600 kDa, with polydisperse multimers frequently measuring at 2,000 kDa or more, all as estimated by comparison to molecular weight standards on SDS tris-acetate 3-8% polyacrylamide gels. Of the total glycosylations, about half of the molecule contain two sugar units (GalNAc-Gal), and half three sugar units (GalNAc-Gal-Sialic acid.

Any one or more of various native and recombinant PRG4 proteins and isoforms may be utilized in the various embodiments described herein. For instance, U.S. Pat. Nos. 6,433,142; 6,743,774; 6,960,562; 7,030,223, and 7,361,738 disclose how to make various forms of human PRG4 expression product, each of which is incorporated herein by reference. Preferred for use in the practice of the invention is full length, glycosylated, recombinant PRG4, or lubricin, expressed from CHO cells. This protein comprises 1404 amino acids (see FIG. 6; SEQ ID NO:1) including a central exon comprising repeats of the sequence KEPAPTT variously glycosylated with O-linked β (1-3) Gal-GalNAc oligosaccharides, and including N and C-terminal sequences with homology to vitronectin. The molecule is polydisperse with the glycosylation pattern of individual molecules varying, and can comprise monomeric, dimeric, and multimeric species.

As used herein, the term "PRG4" is used interchangeably with the term "lubricin." Broadly, these terms refer to any functional isolated or purified native or recombinant properly glycosylated PRG4 proteins, homologs, functional fragments, isoforms, and/or mutants thereof. All useful molecules comprise the sequence encoded by exon 6, or homologs or truncated versions thereof, for example, versions with fewer repeats within this central mucin-like KEPAPTT-repeat domain, together with 0-linked glycosylation. All useful molecules also comprise at least the biological active portions of the sequences encoded by exons 1-5 and 7-12, i.e., sequences responsible for imparting to the molecule its affinity for ECM and endothelial surfaces. In certain embodiments, a preferred PRG4 protein has an average molar mass of between 50 kDa and 500 kDa, preferably between 224 to 467 kD, comprising one or more biological active portions of the PRG4 protein, or functional fragments, such as a lubricating fragment, or a homolog thereof. In a more preferred embodiment, a PRG4 protein comprises monomers of average molar mass of between 220 kDa to about 280 kDa.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and expressed in a host cell for producing recombinant PRG4 protein, and isolated from the cell culture supernatant.

Particular forms of PGR4 constructs may readily be tested for their ability to inhibit chemotaxis and cell motility effectively ex vivo. A wide variety of qualitative and quantitative assay techniques are known which permit determination of whether cell motility is interrupted and to measure the intensity of the responses. See, for example, the seminal work of Boyden, The Chemotactic Effect Of Mixtures Of Antibody And Antigen On Polymorphonuclear Leucocytes, J Exp Med. 1962 Feb. 28; 115(3): 453-466.

For use in the practice of the invention PRG4 may be formulated in a carrier, e.g., suspended in phosphate buffered saline, at concentrations ranging from 1 µg/mL to 10 mg/mL, and more preferably, 100-500 µg/mL. Depending on the specific use, PRG4 is administered parenterally e.g., by injection, daily, weekly, or monthly. It may be administered for systemic distribution through the vasculature, or locally within the vasculature during the course of vascular surgery such as balloon angioplasty and/or stent insertion. It may be injected into a body compartment, e.g., during endoscopic or open wound surgery. Its effect in each case is to bind to cellular or ECM surfaces resulting in inhibition of cell motility and chemotaxis. In yet other embodiments, PRG4 is combined with other components of a boundary lubrication system such as hyaluronic acid (HA), anticoagulants such as heparin, GAGs such as chondroitin sulfate or heparan sulfate, or TIMPs (Tissue Inhibitor of Metalloproteinase), preferably TIMP1, TIMP2, TIMP3, or TIMP4.

Such PRG4 compositions may be used in the following ways to achieve the following effects.

Inhibition of Atherosclerosis

A variety of studies have revealed that atherosclerosis is found in regions of low shear stress within the arterial vasculature. In such locations, a reduction in endothelial nitric oxide synthase production, and concomitant upregulation of VCAM-1 adhesion factors leads to an increase in the adhesion of monocytes in atherosclerotic plaques. (Cheng C., et al. Cell Biochemistry and Biophysics, 2004; 41:279-294). This increase may be traced to an accumulation of macrophages. The present embodiment takes advantage of the ability of PRG4 to inhibit and indeed to almost entirely prevent macrophage accumulation (FIGS. 5A-C), thereby to interrupt the formation and growth of atherosclerotic plaques, and further to reduce the likelihood of plaque rupture.

In the present embodiment, PRG4 injected throughout the vasculature also binds up- and downstream from the plaque, where macrophages tend to accumulate, masking adhesion factors, reducing flow instabilities, preventing particle aggregation and therefore preventing further macrophage association through these factors in addition to its adhesive properties.

Mitigation of Restenosis and Thrombosis in Stent Surgery and Balloon Angioplasty Restenosis is caused in part by low shear stress that tends to encourage macrophage accumulation. In turn, macrophages mediate dissolution of the elastic membrane, and eventually lead to neointimal hyperplasia, increased expression of vascular cell adhesion molecule-1, and decreased nitric oxide production. In contrast, higher shear stress reduces macrophage accumulation and elastic membrane proteolysis (Carlier S G, et al. Circulation 2003; 107:2741-2746). Accordingly, in one embodiment of the invention, PRG4 injected into the circulatory system or irrigated into the intravascular surgical site during surgery, locally binds to the endothelium and exposed extracellular matrix. This serves to inhibit or prevent macrophage accumulation, improve shear mechanotransduction through a "reconstituted" glycocalyx, and to restore proper endothelial gene expression with the result that restenosis is inhibited significantly.

Mitigation of Metastasis

In the first order approximation, metastatic tumor cells require functioning cell motility mechanisms to achieve migration and invasion. Cancer cell migration is similar to normal migration, although in a more random fashion. The metastatic cell extends filopodia or broad lamellipodia, which adhere to extracellular matrix or to adjacent cells through transmembrane receptors to the actin cytoskeleton, upon which the cell pulls itself in the direction of the adhered protrusion, or as described by Lauffenburger D A et al., motility requires morphological polarization, membrane extension, formation of cell—substratum attachments, contractile force and traction, and release of attachments (Lauffenburger D A, et al. Cell 1996; 84(3):359-369 and Hongyu Z, Crit Rev Eukaryot Gene Expr. 2010; 20(1): 1-16). Essentially, cancer cells crawl by extending adherent fingers and pulling themselves forward. While typically it is believed that only malignant tumors metastasize, it is now thought that non-malignant tumors may also be capable of metastasis. Accordingly, the method is applicable to both malignant and non-malignant neoplastic cells. According to the invention, PRG4, a potent boundary lubricant is injected to the periphery in the space where a tumor has been excised, or around an otherwise inoperable or located solid tumor, or within the circulatory system to coat the cellular interface and prevent cancer cells from forming cell—substratum attachments. According to this embodiment, the objective is to provide PRG4 as a motility inhibitor such that the tumor cells cannot attach, cannot crawl, and therefore cannot achieve migration or invasion. It is also recognized that tumors typically engage in extensive intravasation and extravasation, followed by growth and angiogenesis to repeat the process of metastasis. In the current embodiment, systemic or locally applied PRG4 is used to prevent intravasation or extravasation of tumor cells.

A series of studies also suggest that there is a strong association between thrombosis and the progression of cancer, with some studies suggesting that hijacking of the coagulation system may be critical for the survival and spread of the tumor cells; in particular, fibrin and platelets seem to prevent clearing of tumor cells by natural killer cells (Palumbo J S, et al. Blood 2005; 105: 178-85, Bakewell S J, et al. PNAS 2003; 100:14205-14210, Lazo-Langer A, et al., Journal of Thrombosis and Haemostasis, 2007; 5:729-737). Clinical studies have also demonstrated that fibrinogen deficient animal models reduced the incidence of spontaneous macroscopic metastases in the lung and regional lymph nodes, although primary tumor growth and angiogenesis were unaffected (Palumbo J S, et al., Cancer Res 2002; 62:6966-6972). It has also been hypothesized that tumor cells may use local platelet-fibrin depositions to support sustained adhesions of tumor cells within high shear environments, and provide a means for cell proliferation (Palumbo J S, et al. Blood 2005; 105: 178-85). The invention therefore makes use of the ability of PRG4 to almost entirely inhibit the associations of platelets and fibrin (FIGS. 2A-B, 3A-C) to interrupt the metastatic potential of the circulating or solid tumor cells. In addition, the current invention suggests that the boundary properties of a PRG4 coated surface may also shield selectin and integrin mediated platelet activation that is critical to tumor invasion. In one preferred embodiment, PRG4 protein may be injected around the site of an inoperable solid tumor, e.g., a poorly located brain tumor or mass near vital organs in the throat, to minimize metastatic potential of the tumor, and to prevent extravasation of tumor cells into the surrounding compartments. In particular, the invention contemplates prevention or reduction in extravasation and metastasis of primary tumors to the lungs, lymph, liver, bone and brain as these are the most common locations of metastatic tumors.

For example, in one specific embodiment of the invention, lubricin is used to treat, alleviate, or prevent bone metastasis, also known as metastatic bone disease, which results from invasion into the bone of a primary tumor. Bone tissue is a common location for cancer metastasis. The primary tumor causing metastasis may be, for example, lung cancer, prostate cancer, or breast cancer. Treatment of bone metastasis, according to the invention, involves administration of lubricin to a patient suffering from or at risk of developing bone metastasis. Lubricin may be administered to a patient as a pretreatment, for example to prevent or reduce the likelihood of bone metastasis when a non-bone primary tumor has been diagnosed in the patient. Lubricin may also be administered to a patient to prevent, treat, or alleviate bone metastasis in conjunction with administration of a chemotherapeutic agent or radiation treatment to treat a primary tumor or a metastatic cancer. According to one embodiment, the lubricin is administered locally to the bone by injection at the site of metastasis or potential metastasis or it is administered systemically to the patient. In one embodiment, the patient is preferably a human patient.

Lubricin may also be used to treat or prevent ovarian cancer metastasis. It is believed that ovarian cancer metastasizes by seeding tumor cells onto the mesothelial layer lining the peritoneum. Accordingly, in one embodiment, lubricin is administered to a patient having ovarian cancer. In one embodiment, the lubricin is administered systemically, while in another embodiment, the lubricin is administered to the peritoneum in the region of an ovarian tumor in the patient. The patient, in one embodiment, is a human patient.

A non-limiting of list of cancers for which metastasis may be prevented or reduced by administration of lubricin according to the invention include adrenal cancer, anal cancer, bile duct cancer, bladder cancer, bone cancer, brain/CNS cancer, basal cell skin cancer, breast cancer, Castleman disease, cervical cancer, colorectal cancer, endometrial cancer, esophagus cancer, dermatofibrosarcoma protuberans, Ewing family of tumors, eye cancer, gallbladder cancer, gastrointestinal carcinoid tumors, gastrointestinal stromal tumor (GIST), gastric cancer, gestational trophoblastic disease, glioma, glioblastoma, head and neck cancer, hodgkin disease, Kaposi sarcoma, kidney cancer, laryngeal and hypopharyngeal cancer, leukemia, lung cancer, liver cancer, lymphoma, malignant mesothelioma, Merkel cell carcinoma, melanoma, multiple myeloma, myeloma, myelodysplastic syndrome, nasal cavity and paranasal sinus cancer, nasopharyngeal cancer, neuroendocrine cancer, neuroblastoma, Non-Hodgkin lymphoma, oral cavity and oropharyngeal cancer, osteosarcoma, ovarian cancer, pancreatic cancer, penile cancer, pituitary Tumors, prostate cancer, renal cancer, retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, uterine sarcoma, vaginal cancer, vulvar cancer, Waldenstrom macroglobulinemia, and Wilms tumor.

Prevention of Fibrosis

Fibrosis occurs when fibroblasts produce connective tissue, i.e., scar tissue, sometimes in excess, in an organ or tissue. Generally, fibrosis occurs as a result of the reparative process. When a tissue is injured, for example, through surgical means or other physical injury, macrophages are recruited to the site of the injury and, along with the damaged tissue, produce TGF-beta, which signals fibroblasts to produce connective tissue to close the wound. In some cases, fibrosis occurs in the absence of a surgical insult or physical injury to the tissue. For example, viral or bacterial infections or genetic abnormalities may lead to fibrosis. Many instances of fibrosis are idiopathic. Nonetheless, whether caused by physical injury or not, the invention provides that fibrosis may be alleviated, prevented or slowed through the use of PRG4. Essentially, PRG4 provides a mechanical barrier to prevent or limit macrophage accumulation at the site of tissue injury to prevent or limit fibrosis, or in the case of an organ or tissue that is already fibrotic, to limit or retard the progress of fibrosis by reducing or preventing the accumulation of further macrophages at the site.

According to one embodiment, the invention provides a method for preventing, alleviating or slowing fibrosis by administering to a patient at risk of developing fibrosis or experiencing fibrosis in an organ or tissue an effective amount of PRG4 in a pharmaceutical carrier. The PRG4 may be administered to the patient directly or indirectly by injection. For example, the PRG4 may be administered systemically to the vasculature of the patient or it may be administered locally or topically to the site at risk of developing fibrosis or where fibrosis is present. The site of local administration may be an organ or tissue or the surface of the organ or tissue.

In some instances, as discussed above, fibrosis is not the result of a surgical or physical tissue injury, but rather is the result of another cause such as infection, underlying genetic abnormalities, or idiopathic. Some examples of fibrosis that are not necessarily caused by surgical insults, include cirrhosis of the liver, pulmonary fibrosis, cardial fibrosis, mediastinal fibrosis, arthrofibrosis, myelofibrosis, nephogenic systemic fibrosis, keloid fibrosis, scelorderma fibrosis, cystic fibrosis, renal fibrosis, lymphatic tissue fibrosis, arterial, capillary, and vascular fibrosis, and pancreatic fibrosis.

In another embodiment, the invention provides a method for preventing or slowing fibrosis at the site of a surgical incision in a patient in order to maintain patency of the surgical incision by administering to the patient an effective amount of PRG4 in a pharmaceutically acceptable carrier. The PRG4 may be administered to the patient directly or indirectly by injection. For example, the PRG4 may be administered systemically to the vasculature of the patient or it may be administered locally or topically to the site of the surgical incision.

For example, the purpose of some surgeries is to provide an opening in the tissue that does not close. This can be useful in order to provide drainage from a tissue or organ to relieve pressure or to remove fluid, to evacuate waste products, or to place a device that will eventually be removed, i.e., a temporary device where it is not desirable for the device to "heal in." Accordingly, in these instances, providing PRG4 locally at the site of the surgical incision helps prevent or reduce the instance of fibrosis at the site.

Surgical methods for providing an incision not intended to close include surgically produced stomas such as dacryocystorhinostomy (a surgically formed connection between the nose and lacrimal sac); gastrointestinal stomas such as a cecostomy, colostomy, duodenostomy, ileostomy, jejunostomy; esophagostomy; gastrostomy; cholecystostomy; choledochostomy; sclerostomy; tracheostomy, urostomy, nephrostomy, ureterostomy, vesicostomy, cystostomy, and enterostomy; an ileoanal reservoir; a site for placement of a percutaneous catheter or stent; or surgical windows (both exterior and interior) in the skull and sinuses. For example, the Caldwell-Luc operation relieves chronic sinusitis by creating a "window" to connect the maxillary sinus with the nose, thus improving drainage of the maxillary sinus, one of the cavities beneath the eye.

Further, the invention provides methods to maintain separation of tissue, organs and/or tendons after an adhesiolysis or surgical release. Adhesions may form as the result of prior surgery or from other conditions that permit scar tissue to form between tissues and/or organs that are otherwise not connected. Adhesions may be surgically "lysed" or cut. Surgical release may be performed to release tendons and connective tissue that are improperly attached or where the attachment otherwise causes pain. Accordingly, the invention provides methods to prevent reconnection of tissues, tendons and/or organs that are separated by adhesiolysis or surgical release by administering PRG4. The PRG4 may be administered to the patient directly or indirectly by injection. For example, the PRG4 may be administered systemically to the vasculature of the patient or it may be administered locally or topically to the site of the adhesiolysis or surgical release. In the case of carpal tunnel syndrome, PRG4 may be administered to the site of a transection of retinaculum.

Improvements in Trabeculoplasty or Trabeculectomy

The current embodiment provides for irrigation and or injection of PRG4 to prevent restenosis of trabeculoplasty or trabeculectomy in the human eye performed during an ocular surgery, for example, to treat glaucoma by relieving pressure in the eye. The incision in or removal of part of the trabecular mesh permits aqueous humor to drain from the eye, relieving pressure. However, the incision in the trabecular mesh may be prone to closure and fibrosis due to exposure of damaged epithelium and migration of macrophages to the site to promote tissue repair.

Accordingly, one embodiment of this invention includes the use of PRG4 during glaucoma surgery to prevent migration of macrophages and other cells involved in tissue repair to the incision. Accordingly, in one preferred embodiment, the boundary lubricating and boundary film forming abilities of PRG4 coated tissues is used to effect a minimally invasive trabeculoplasty or trabeculectomy. In one aspect of this method, rather than creating a fornix- or limbus-based conjunctival flap, or implanting a subchoroidal stent in higher risk patients, very small needles (e.g., 27 to 34 gauge) filled with PRG4 are passed through the trabecular meshwork into the anterior chamber, followed by retraction with delivery of the PRG4 to fill and coat the channel created by the syringe with boundary lubricant. By repeating this process in a radial fashion, minimal damage is done to the eye, no foreign substance is introduced into the eye, drainage can be distributed radially, reducing the need for blebs, additional channels can easily be added if more drainage is necessary, and the PRG4 coated channels prevent restenosis.

Increase in Nitric Oxide Production

The current embodiment also provides for replenishing the vascular glycocalyx so to better transmit shear stress to the endothelial cells below. This serves to generally enhance vascular health and maintenance, and to preserve endothelial NO production. One interesting sequelae of poor NO production is the inability to sustain a high quality or sustained erection. In particular, nitric oxide binds to guanylate cyclase receptors, upregulating cGMP, causing vasodilation, corpus cavernosal smooth muscle relaxation and eventually penile erection (Webb, D. J., et al. Am. J. Cardiol 1999; 83(5A): 21C-28C). In the current embodiment, replenishment/enhancement of the vascular endothelial glycocalyx with PRG4 leads to better, more sustained erections. The current embodiment also envisions use of external, epithelial PRG4 to achieve complementary effects.

Mitigation of Transplant Rejection

Traditional immunosuppressive therapy, e.g., corticosteroids, calcineurin inhibitors, mTOR inhibitors, and antiproliferatives following tissue transplant surgery carries a variety of unfortunate side effects. One embodiment of the current invention uses periodic injections of PRG4 around the transplanted tissue to create a mechanical barrier based on boundary film formation to dramatically reduce the incidence of hyperacute, acute and chronic rejection. PRG4 coated surfaces prevent cellular and humoral immune cells from binding to and recognizing the transplant, but allows the immune system to function normally in the rest of the body. According to the invention, the method may be used to treat transplanted heart, liver, kidney, lung, skin or tendon or any other transplanted organ or tissue.

Inhibition of Thrombosis

PRG4 may be useful for inhibiting formation of intravascular thrombosis which may obstruct blood vessels, resulting in such events as stroke, myocardial infarction, pulmonary embolism, or blockage of blood vessels to other parts of the body.

Figure 2A:
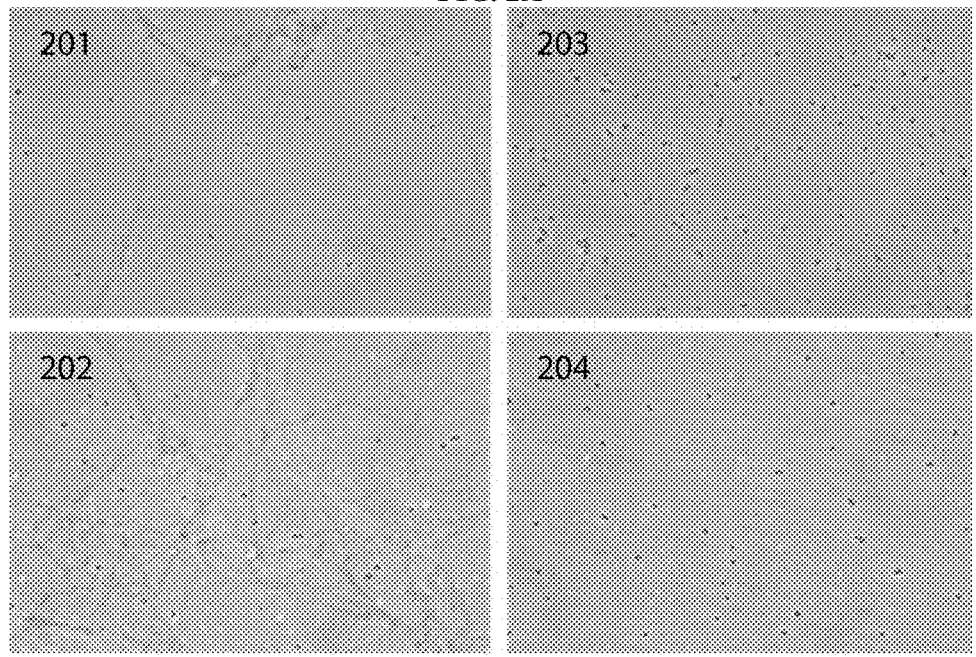
FIG. 2A shows pictures taken with a bright field microscope of plates coated with fibrin and platelets (Panel 201—after 24 hours; Panel 202—after 48 hours) and plates coated with fibrin, platelets, and PRG4 (Panel 203—after 24 hours; Panel 204—after 48 hours). Dark spots represent non-adhered platelets.

To demonstrate the anti-thrombotic effect of PRG4, the ability of PRG4 to interrupt platelet adhesion to a fibrin surface was tested. The results are shown in FIGS. 2A-B.

Plastic cell culture dishes were coated with 10 µL of thrombin at 50 U/mL and 120 µL fibrinogen at 270 mg/mL, suspended in 10 mL of water, and incubated for 3 hours at 37° C. After 3 hours, dishes were rinsed with autoclaved deionized water. Next, 10 µL of PRG4 at 1.42 mg/mL in 10 mL of water were added to the dish shown in panel 203 and 204 and incubated at 37° C. for 2 hours. Following the incubation, dishes were washed again with autoclaved deionized water and $6\times10^5$ platelets in sterile PBS were added to each dish, mixed and incubated at room temperature.

Panel 201 shows a fibrin only dish at 24 hours, while panel 202 shows fibrin only dish at 48 hours; note that in both fibrin-only panels, there are few non-adhered platelets observable in the bulk solution (e.g., the small dark circles). Panel 203 shows a PRG4 and fibrin dish at 24 hours, while panel 204 shows PRG4 and fibrin dish at 48 hours, which have a significantly higher number of non-adhered platelets.

Figure 2B:
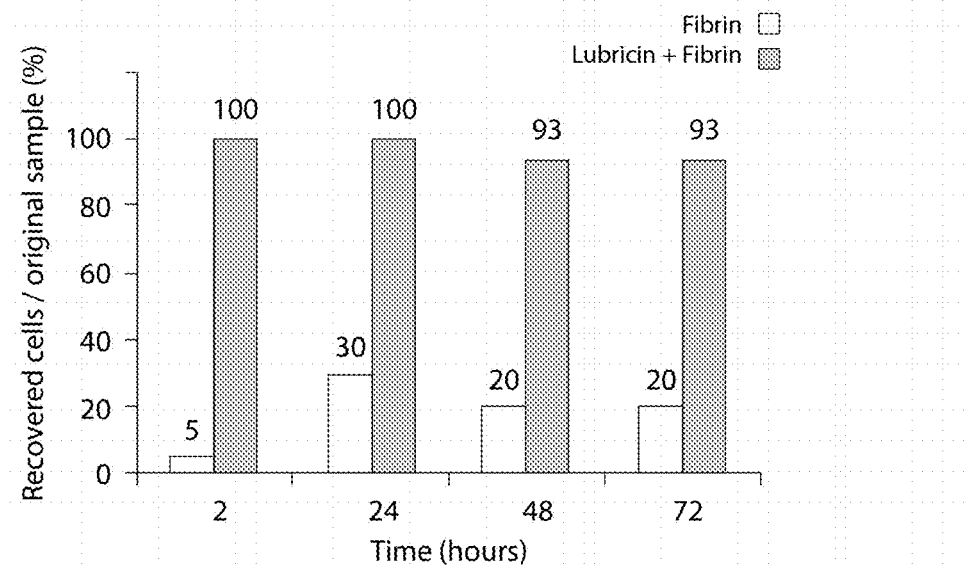
FIG. 2B is a bar graph quantifying the effect of lubricin on platelet adhesion in the plates shown in FIG. 2A. As shown, the level of platelet recovery (i.e., non-adhered platelets) was dramatically higher from samples where lubricin was present.

The effect of PRG4 on platelet adhesion (quantifying the recovery of cells as a percentage of the original sample) is shown in FIG. 2B. As illustrated, the exceptional recovery of platelets from PRG4 coated dishes indicates PRG4's ability to prevent platelets from binding to the fibrin surface.

Figure 3A:
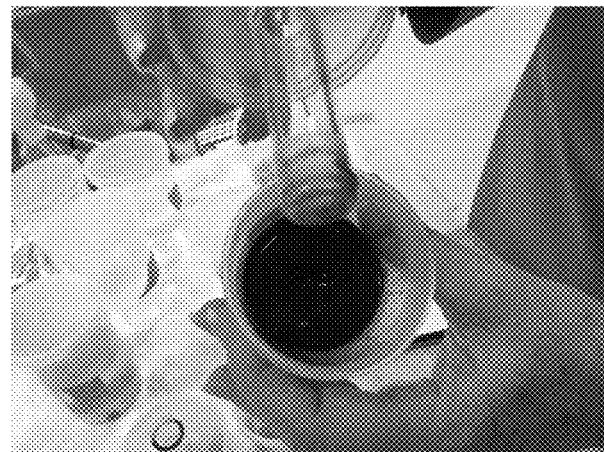
FIGS. 3A-C show clotting of blood in CLOTMASTER™ Hula Cups of untreated blood (FIG. 3A), blood treated with phosphate buffered saline (PBS.
Figure 3B:
Figure 3C:

In a second experiment, PRG4's ability to inhibit thrombogenesis was observed in vitro by testing clot formation in the presence and absence of PRG4. Three samples of 30 mL of whole blood were obtained via venipuncture and placed in CLOTMASTER™ Hula Cups (Pierce Surgical Corp. Stowe, Vt.) with a sintered glass core. To one sample 1.5 mL of phosphate buffered saline (PBS) was added as a negative control to show the result when no anticoagulant effect is expected; to the second sample 1.5 mL rhPRG4 080 at a concentration of 1 mg/mL was added. The third sample was used as a control and was untreated. Each sample was swirled for 60 seconds; swirling stopped and the containers remained static for 9 minutes to promote clot formation. Clot quality was then assessed and clots were decanted and placed in formalin. The results are shown in FIGS. 3 A-C where the photographs show that in the control clot formation was observed as can be seen on the sintered glass core and in the bottom of the cup as a viscous mass (FIG. 3A). For the PBS sample, clot formation occurred as is evidenced by the viscous mass in the bottom of the cup (FIG. 3B). In contrast, no clot formation was observed in the presence of as the blood is still fluid and flowed to one side of the cup when tipped (FIG. 3C). This data strongly demonstrates the anti-thrombotic properties of PRG4.

Figure 4A:
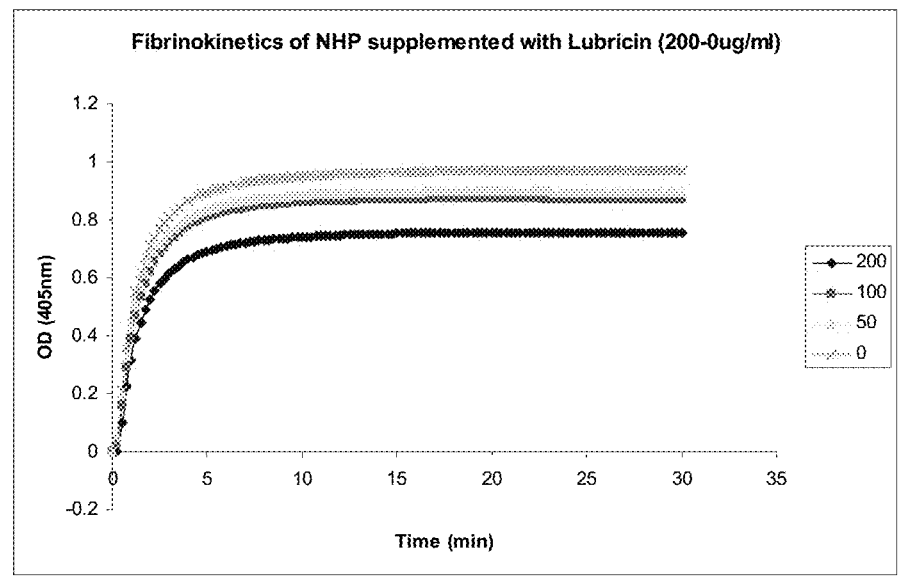
FIGS. 4A-B are line graphs presenting data showing the fibrokinetics of samples of normal human plasma (NHP.
Figure 4B:
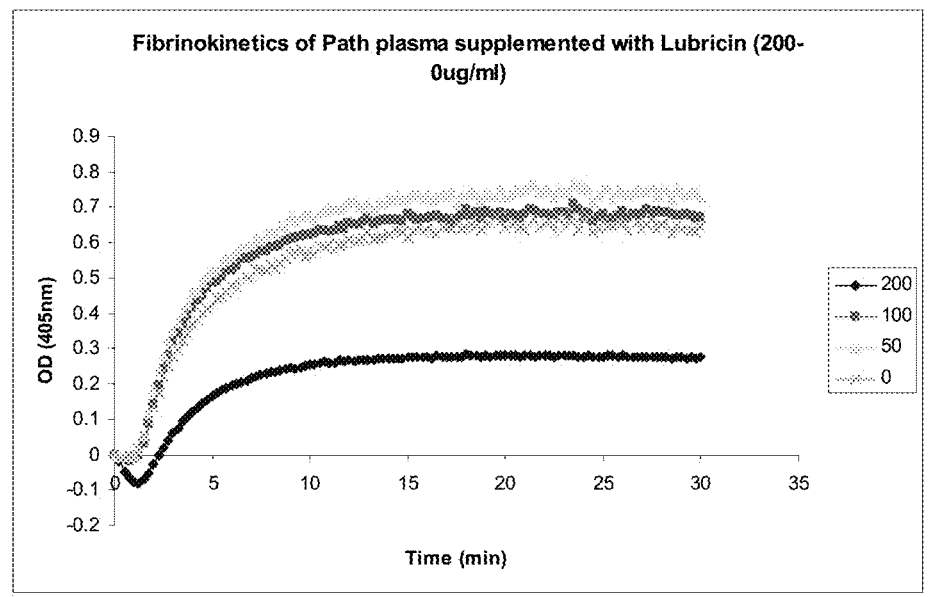

In a third experiment, the effect of PRG4 on the fibrokinetic profile of normal and pathological plasma was tested. Normal human plasma ("NHP") was supplemented with lubricin (2 mg/mL) at a 1:10 dilution. Subsequent 1:2 and 1:4 dilutions were made in normal human plasma. Pooled plasma from liver disease patients ("Path plasma") was also supplemented with lubricin (2 mg/mL) at a 1:10 dilution. Subsequent 1:2 and 1:4 dilutions were made in pooled liver disease plasma. The formation of a fibrin clot was tested by reading optical density at 405 nm for 30 minutes at 15 second intervals on 200 µL plasma samples of each dilution mixed with 25 µL $CaCl_2$ (0.25 mM) and 25 µL thrombin (5 U/mL). Samples with no added lubricin (0 mg/mL) were used as controls. As shown in FIGS. 4A and 4B, lubricin at a concentration of 200 µg/mL decreased optical density in both normal human plasma and pathologic plasmas which indicates that the rate of fibrin (clot) formation was decreased in each sample (see bottom data line in each of FIGS. 4A and 4B). These experiments suggests that lubricin interferes with fibrin clot formation. Accordingly, this data suggests that lubricin has antithrombotic properties.

The anti-thrombotic properties of PRG4 make it useful as an anticoagulant. For example, PRG4 may be used in diagnostic applications as an anticoagulant. For example, in one embodiment, PRG4 is used to coat containers and vials designed for capturing or containing or processing a blood sample. In another embodiment, dialysis equipment, surgical equipment, stents or other devices for implantation in a human or animal body are coated with lubricin to act as an anticoagulant.

In another embodiment, PRG4 is administered to a patient, for example, by injection or another administration method described herein as an anticoagulant therapy. For example, PRG4 may be administered to a patient to prevent or reduce clot formation in a patient suffering from or at risk of thrombosis from deep vein thrombosis; pulmonary embolism; a clotting disorder such as Factor V Leiden, Prothrombin 20210 mutation, hyperhomocysteinemia, Protein C deficiency, Protein S deficiency, Antithrombin deficiency, Von Willebrand Factor disorder, or elevated level of procoagulant protein such as VIII, IX, XI, VII, fibrinogen, and Von Willebrand factor; a heart condition such as atrial fibrillation, mechanical or prosthetic valve, or patent foramen ovale. Administration of PRG4 prevents or reduces clot formation in such patients. PRG4 may be administered systemically or locally to a site at risk of thrombosis or where a thrombosis is present. In these instances, PRG4 may be administered to a patient in conjunction with another anticoagulant therapy such as heparin, warfarin, coumarin, or dabigatran. PRG4 may be administered as a prophylactic in patients with the aforementioned conditions to prevent clotting due to the patient's condition.

Administration of Lubricin

Generally, a therapeutically effective amount of lubricin for administration systemically is in the range of 0.1 mg/kg to 100 mg/kg, or 1 mg/kg to 100 mg/kg, or 1 mg/kg to 10 mg/kg. In one embodiment, the dose of lubricin is between 0.25 mg/kg and 2.5 mg/kg or is between 0.25 and 3.0 mg/kg. The amount administered will depend on variables such as the type and extent of the condition to be treated, the overall health of the patient, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. The optimal dose can be determined by routine experimentation. For parenteral administration a dose between 0.1 mg/kg and 100 mg/kg, alternatively between 0.5 mg/kg and 50 mg/kg, alternatively, between 1 mg/kg and 25 mg/kg, alternatively between 2 mg/kg and 10 mg/kg, alternatively between 5 mg/kg and 10 mg/kg is administered and may be given, for example, once weekly, once every other week, once every third week, or once monthly per treatment cycle.

For administration, lubricin is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art. Useful formulations can be prepared by methods well known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfate; chelating agents such as EDTA; buffers such as acetates, citrates or phosphates; and agents for the adjustment of tonicity such as sodium chloride or dextrose.

Lubricin for administration can be presented in a dosage unit form and can be prepared by any suitable method and should be formulated to be compatible with its intended route of administration. Examples of routes of administration are oral, intravenous (IV), intradermal, subcutaneous, intramuscular, inhalation, transdermal, topical, transmucosal, rectal administration, parenteral, intranasal, topical, oral, or local administration, such as by a transdermal means, for therapeutic treatment. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration.

For intravenous administration, suitable carriers include physiological saline, bacteriostatic water, Cremophor EL™

(BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Other features and advantages of the invention will be apparent from the following description of the preferred embodiments thereof and from the claims. These and many other variations and embodiments of the invention will be apparent to one of skill in the art upon a review of the description and examples.

---

What is claimed is:

1. A method of maintaining or improving circulatory system function in a patient comprising administering directly or indirectly to the circulatory system of said patient a composition comprising PRG4 in an amount sufficient to form a boundary lubrication film of PRG4 at a stressed endothelial surface or plaque within the patient's circulatory system.

2. The method of claim 1, wherein administering the PRG4 improves circulatory system function by reducing flow instability within the subject's circulatory system.

3. A method of inhibiting or reducing vascular thrombus formation in a patient comprising administering directly or indirectly to the circulatory system of said patient a composition comprising PRG4 in an amount sufficient to form a boundary lubrication film of PRG4 on fibrin and/or platelets present therein.

4. The method of claim 3, wherein the PRG4 is administered at a dose of between 0.3 mg/kg and 3.0 mg/kg.

5. A method of reducing or inhibiting vascular restenosis in a patient after an intravascular procedure comprising administering to the circulatory system of said patient a composition comprising PRG4 in an amount sufficient to form a boundary lubricating film of PRG4 at an endothelial surface at a site of said intravascular procedure.

6. The method of claim 5, wherein the intravascular procedure is a balloon angioplasty or a stent insertion.

7. The method of claim 5, wherein the PRG4 is administered at a dose of between 0.3 mg/kg and 3.0 mg/kg.

8. The method of claim 1, wherein the PRG4 is administered at a dose of between 0.3 mg/kg and 3.0 mg/kg.

9. The method of claim 1, wherein the administering is by injection to the patient.

10. The method of claim 9, wherein the injection is a systemic intravenous injection to the circulatory system of the patient.

11. The method of claim 9, wherein the injection is a localized injection at the stressed endothelial surface or plaque within the patient's circulatory system.

12. The method of claim 1, wherein the composition further comprises a physiologically compatible vehicle.

13. The method of claim 3, wherein the PRG4 is administered by injection to the patient.

14. The method of claim 13, wherein the injection is a systemic intravenous injection to the circulatory system of the patient.

15. The method of claim 13, wherein the injection is a localized injection at a site of thrombosis or at a site at risk of developing a thrombosis.

16. The method of claim 3, wherein the composition further comprises a physiologically compatible vehicle.

17. The method of claim 5, wherein the administering is by injection to the patient.

18. The method of claim 17, wherein the injection is a systemic intravenous injection to the circulatory system of the patient.

19. The method of claim 17, wherein the injection is a local injection at the site of the intravascular procedure.

20. The method of claim 5, wherein the composition further comprises a physiologically compatible vehicle.

21. The method of claim 1, wherein the PRG4 comprises the amino acid sequence of residues 25-1404 of SEQ ID NO:1.

22. The method of claim 3, wherein the PRG4 comprises the amino acid sequence of residues 25-1404 of SEQ ID NO:1.

23. The method of claim 5, wherein the PRG4 comprises the amino acid sequence of residues 25-1404 of SEQ ID NO:1.

* * * * *

SEQUENCE LISTING

<160> NUMBER OF SEQ ID NOS: 3

<210> SEQ ID NO 1
<211> LENGTH: 1404
<212> TYPE: PRT
<213> ORGANISM: Homo sapiens

<400> SEQUENCE: 1

```
Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
            115                 120                 125

Ile Lys Ser Thr Thr Lys Arg Ser Pro Lys Pro Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
```

-continued

```
            275                 280                 285
Thr Thr Thr Thr Asn Lys Gln Thr Ser Thr Asp Gly Lys Glu Lys Thr
290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
                340                 345                 350

Thr Thr Pro Lys Glu Pro Ala Ser Thr Thr Pro Lys Glu Pro Thr Pro
                355                 360                 365

Thr Thr Ile Lys Ser Ala Pro Thr Thr Pro Lys Glu Pro Ala Pro Thr
                370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
                420                 425                 430

Lys Glu Pro Ala Pro Thr Thr Pro Lys Lys Pro Ala Pro Thr Thr Pro
                435                 440                 445

Lys Glu Pro Ala Pro Thr Thr Pro Lys Glu Pro Thr Pro Thr Thr Pro
450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
                500                 505                 510

Glu Pro Ser Pro Thr Thr Pro Lys Glu Pro Ala Pro Thr Thr Thr Lys
                515                 520                 525

Ser Ala Pro Thr Thr Thr Lys Glu Pro Ala Pro Thr Thr Thr Lys Ser
530                 535                 540

Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
                580                 585                 590

Ala Pro Thr Thr Thr Lys Lys Pro Ala Pro Thr Thr Pro Lys Glu Pro
                595                 600                 605

Ala Pro Thr Thr Pro Lys Glu Thr Ala Pro Thr Thr Pro Lys Lys Leu
                610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
                675                 680                 685

Ala Pro Thr Thr Pro Lys Glu Pro Ala Pro Thr Thr Pro Lys Glu Thr
                690                 695                 700
```

-continued

```
Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
            740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
    770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
                820                 825                 830

Glu Pro Ala Pro Thr Thr Pro Lys Lys Pro Ala Pro Thr Thr Pro Glu
            835                 840                 845

Thr Pro Pro Pro Thr Thr Ser Glu Val Ser Thr Pro Thr Thr Thr Lys
        850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910

Thr Thr Ala Lys Asp Lys Thr Thr Glu Arg Asp Leu Arg Thr Thr Pro
            915                 920                 925

Glu Thr Thr Thr Ala Ala Pro Lys Met Thr Lys Glu Thr Ala Thr Thr
930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
                980                 985                 990

Thr Thr Thr Glu Ile Met Asn Lys Pro Glu Glu Thr Ala Lys Pro Lys
            995                 1000                1005

Asp Arg Ala Thr Asn Ser Lys Ala Thr Thr Pro Lys Pro Gln Lys
    1010                1015                1020

Pro Thr Lys Ala Pro Lys Lys Pro Thr Ser Thr Lys Lys Pro Lys
    1025                1030                1035

Thr Met Pro Arg Val Arg Lys Pro Lys Thr Thr Pro Thr Pro Arg
    1040                1045                1050

Lys Met Thr Ser Thr Met Pro Glu Leu Asn Pro Thr Ser Arg Ile
    1055                1060                1065

Ala Glu Ala Met Leu Gln Thr Thr Thr Arg Pro Asn Gln Thr Pro
    1070                1075                1080

Asn Ser Lys Leu Val Glu Val Asn Pro Lys Ser Glu Asp Ala Gly
    1085                1090                1095

Gly Ala Glu Gly Glu Thr Pro His Met Leu Leu Arg Pro His Val
    1100                1105                1110
```

| | | | | | | | | | | |
|---|---|---|---|---|---|---|---|---|---|---|
| Phe | Met | Pro | Glu | Val | Thr | Pro | Asp | Met | Asp | Tyr | Leu | Pro | Arg | Val |
| 1115 | | | | | 1120 | | | | | 1125 | | | | |
| Pro | Asn | Gln | Gly | Ile | Ile | Ile | Asn | Pro | Met | Leu | Ser | Asp | Glu | Thr |
| 1130 | | | | | 1135 | | | | | 1140 | | | | |
| Asn | Ile | Cys | Asn | Gly | Lys | Pro | Val | Asp | Gly | Leu | Thr | Thr | Leu | Arg |
| 1145 | | | | | 1150 | | | | | 1155 | | | | |
| Asn | Gly | Thr | Leu | Val | Ala | Phe | Arg | Gly | His | Tyr | Phe | Trp | Met | Leu |
| 1160 | | | | | 1165 | | | | | 1170 | | | | |
| Ser | Pro | Phe | Ser | Pro | Pro | Ser | Pro | Ala | Arg | Arg | Ile | Thr | Glu | Val |
| 1175 | | | | | 1180 | | | | | 1185 | | | | |
| Trp | Gly | Ile | Pro | Ser | Pro | Ile | Asp | Thr | Val | Phe | Thr | Arg | Cys | Asn |
| 1190 | | | | | 1195 | | | | | 1200 | | | | |
| Cys | Glu | Gly | Lys | Thr | Phe | Phe | Phe | Lys | Asp | Ser | Gln | Tyr | Trp | Arg |
| 1205 | | | | | 1210 | | | | | 1215 | | | | |
| Phe | Thr | Asn | Asp | Ile | Lys | Asp | Ala | Gly | Tyr | Pro | Lys | Pro | Ile | Phe |
| 1220 | | | | | 1225 | | | | | 1230 | | | | |
| Lys | Gly | Phe | Gly | Gly | Leu | Thr | Gly | Gln | Ile | Val | Ala | Ala | Leu | Ser |
| 1235 | | | | | 1240 | | | | | 1245 | | | | |
| Thr | Ala | Lys | Tyr | Lys | Asn | Trp | Pro | Glu | Ser | Val | Tyr | Phe | Phe | Lys |
| 1250 | | | | | 1255 | | | | | 1260 | | | | |
| Arg | Gly | Gly | Ser | Ile | Gln | Gln | Tyr | Ile | Tyr | Lys | Gln | Glu | Pro | Val |
| 1265 | | | | | 1270 | | | | | 1275 | | | | |
| Gln | Lys | Cys | Pro | Gly | Arg | Arg | Pro | Ala | Leu | Asn | Tyr | Pro | Val | Tyr |
| 1280 | | | | | 1285 | | | | | 1290 | | | | |
| Gly | Glu | Thr | Thr | Gln | Val | Arg | Arg | Arg | Phe | Glu | Arg | Ala | Ile |
| 1295 | | | | | 1300 | | | | | 1305 | | | |
| Gly | Pro | Ser | Gln | Thr | His | Thr | Ile | Arg | Ile | Gln | Tyr | Ser | Pro | Ala |
| 1310 | | | | | 1315 | | | | | 1320 | | | | |
| Arg | Leu | Ala | Tyr | Gln | Asp | Lys | Gly | Val | Leu | His | Asn | Glu | Val | Lys |
| 1325 | | | | | 1330 | | | | | 1335 | | | | |
| Val | Ser | Ile | Leu | Trp | Arg | Gly | Leu | Pro | Asn | Val | Val | Thr | Ser | Ala |
| 1340 | | | | | 1345 | | | | | 1350 | | | | |
| Ile | Ser | Leu | Pro | Asn | Ile | Arg | Lys | Pro | Asp | Gly | Tyr | Asp | Tyr | Tyr |
| 1355 | | | | | 1360 | | | | | 1365 | | | | |
| Ala | Phe | Ser | Lys | Asp | Gln | Tyr | Tyr | Asn | Ile | Asp | Val | Pro | Ser | Arg |
| 1370 | | | | | 1375 | | | | | 1380 | | | | |
| Thr | Ala | Arg | Ala | Ile | Thr | Thr | Arg | Ser | Gly | Gln | Thr | Leu | Ser | Lys |
| 1385 | | | | | 1390 | | | | | 1395 | | | | |
| Val | Trp | Tyr | Asn | Cys | Pro | | | | | | | | | |
| 1400 | | | | | | | | | | | | | | |

<210> SEQ ID NO 2
<211> LENGTH: 5041
<212> TYPE: DNA
<213> ORGANISM: Homo sapiens

<400> SEQUENCE: 2

```
gcggccgcga ctattcggta cctgaaaaca acgatggcat ggaaaacact tcccatttac     60
ctgttgttgc tgctgtctgt tttcgtgatt cagcaagttt catctcaaga tttatcaagc    120
tgtgcaggga gatgtgggga agggtattct agagatgcca cctgcaactg tgattataac    180
tgtcaacact acatggagtg ctgccctgat ttcaagagag tctgcactgc ggagctttcc    240
tgtaaaggcc gctgctttga gtccttcgag agagggaggg agtgtgactg cgacgcccaa    300
tgtaagaagt atgacaagtg ctgtcccgat tatgagagtt tctgtgcaga agtgcataat    360
```

```
cccacatcac caccatcttc aaagaaagca cctccacctt caggagcatc tcaaaccatc      420
aaatcaacaa ccaaacgttc acccaaacca ccaaacaaga agaagactaa gaaagttata      480
gaatcagagg aaataacaga agaacattct gtttctgaaa atcaagagtc ctcctcctcc      540
tcctcctctt cctcttcttc ttcaacaatt tggaaaatca agtcttccaa aaattcagct      600
gctaatagag aattacagaa gaaactcaaa gtaaagata acaagaagaa cagaactaaa       660
aagaaaccta cccccaaacc accagttgta gatgaagctg gaagtggatt ggacaatggt      720
gacttcaagg tcacaactcc tgacacgtct accacccaac acaataaagt cagcacatct      780
cccaagatca acagcaaa accaataaat cccagaccca gtcttccacc taattctgat        840
acatctaaag agacgtcttt gacagtgaat aaagagacaa cagttgaaac taaagaaact      900
actacaacaa ataaacagac ttcaactgat ggaaaagaga agactacttc cgctaaagag      960
acacaaagta tagagaaaac atctgctaaa gatttagcac ccacatctaa agtgctggct     1020
aaacctacac ccaaagctga aactacaacc aaaggccctg ctctcaccac tcccaaggag     1080
cccacgccca ccactcccaa ggagcctgca tctaccacac ccaaagagcc cacacctacc     1140
accatcaagt ctgcacccac cacccccaag gagcctgcac ccaccaccac caagtctgca     1200
cccaccactc ccaaggagcc tgcacccacc accaccaagg agcctgcacc caccactccc     1260
aaggagcctg cacccaccac caccaaggag cctgcaccca ccaccaa gtctgcaccc        1320 accactccca aggagcctgc acccaccacc cccaagaagc ctgccccaac tacccccaag     1380
gagcctgcac ccaccactcc caaggagcct acacccacca ctcccaagga gcctgcaccc     1440
accaccaagg agcctgcacc caccactccc aaagagcctg cacccactgc ccccaagaag     1500
cctgccccaa ctaccccaa ggagcctgca cccaccactc caaggagcc tgcacccacc        1560 accaccaagg agccttcacc caccactccc aaggagcctg cacccaccac caccaagtct     1620
gcacccacca ctaccaagga gcctgcaccc accactacca gtctgcacc caccactccc      1680 aaggagcctt cacccaccac caccaaggag cctgcaccca ccactcccaa ggagcctgca     1740
cccaccaccc ccaagaagcc tgccccaact accccaagg agcctgcacc caccactccc      1800
aaggaacctg cacccaccac caccaagaag cctgcaccca ccgctcccaa agagcctgcc     1860
ccaactaccc ccaaggagac tgcacccacc acccccaaga agctcacgcc caccaccccc     1920
gagaagctcg cacccaccac ccctgagaag cccgcaccca ccaccctga ggagctcgca      1980 cccaccaccc ctgaggagcc acacccacc accctgagg agcctgctcc caccactccc       2040
aaggcagcgg ctcccaacac ccctaaggag cctgctccaa ctacccctaa ggagcctgct     2100
ccaactaccc ctaaggagcc tgctccaact accccctaag gagactgctcc aactacccct    2160 aaagggactg ctccaactac cctcaaggaa cctgcaccca ctactcccaa gaagcctgcc     2220
cccaaggagc ttgcacccac caccaccaag gagcccacat ccaccacctc tgacaagccc     2280
gctccaacta cccctaaggg gactgctcca actacccccta aggagcctgc tccaactacc    2340
cctaaggagc ctgctccaac tacccctaag gggactgctc caactaccct caaggaacct    2400
gcacccacta ctcccaagaa gcctgccccc aaggagcttg cacccaccac caccaagggg     2460
cccacatcca ccacctctga caagcctgct ccaactacac ctaaggagac tgctccaact     2520
acccccaagg agcctgcacc cactaccccc aagaagcctg ctccaactac tcctgagaca     2580
cctcctccaa ccacttcaga ggtctctact ccaactacca ccaaggagcc taccactatc     2640
cacaaaagcc ctgatgaatc aactcctgag ctttctgcag aacccacacc aaaagctctt     2700
```

-continued

```
gaaaacagtc ccaaggaacc tggtgtacct acaactaaga ctcctgcagc gactaaacct    2760
gaaatgacta caacagctaa agacaagaca acagaaagag acttacgtac tacacctgaa    2820
actacaactg ctgcacctaa gatgacaaaa gagacagcaa ctacaacaga aaaaactacc    2880
gaatccaaaa taacagctac aaccacacaa gtaacatcta ccacaactca agataccaca    2940
ccattcaaaa ttactactct taaaacaact actcttgcac ccaaagtaac tacaacaaaa    3000
aagacaatta ctaccactga gattatgaac aaacctgaag aaacagctaa accaaaagac    3060
agagctacta attctaaagc gacaactcct aaacctcaaa agccaaccaa agcacccaaa    3120
aaacccactt ctaccaaaaa gccaaaaaca atgcctagag tgagaaaacc aaagacgaca    3180
ccaactcccc gcaagatgac atcaacaatg ccagaattga accctacctc aagaatagca    3240
gaagccatgc tccaaaccac caccagacct aaccaaactc caaactccaa actagttgaa    3300
gtaaatccaa agagtgaaga tgcaggtggt gctgaaggag aaacacctca tatgcttctc    3360
aggccccatg tgttcatgcc tgaagttact cccgacatgg attacttacc gagagtaccc    3420
aatcaaggca ttatcatcaa tcccatgctt tccgatgaga ccaatatatg caatggtaag    3480
ccagtagatg gactgactac tttgcgcaat gggacattag ttgcattccg aggtcattat    3540
ttctggatgc taagtccatt cagtccacca tctccagctc gcagaattac tgaagtttgg    3600
ggtattcctt cccccattga tactgttttt actaggtgca actgtgaagg aaaaactttc    3660
ttctttaagg attctcagta ctggcgtttt accaatgata taaagatgc agggtacccc    3720
aaaccaattt tcaaaggatt tggaggacta actggacaaa tagtggcagc gctttcaaca    3780
gctaaatata agaactggcc tgaatctgtg tattttttca agagaggtgg cagcattcag    3840
cagtatattt ataaacagga acctgtacag aagtgccctg gaagaaggcc tgctctaaat    3900
tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140
ttttctaaag atcaatacta taacattgat gtgcctagta aacagcaag agcaattact    4200
actcgttctg ggcagaccct atccaaagtc tggtacaact gtccttagac tgatgagcaa    4260
aggaggagtc aactaatgaa gaaatgaata ataaattttg acactgaaaa acattttatt    4320
aataaagaat attgacatga gtataccagt ttatatataa aaatgttttt aaacttgaca    4380
atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc ttttttgtgac acaagtacaa    4680
tctaaaagtt atattggaaa acatggaaat attaaaattt tacacttta ctagctaaaa    4740
cataatcaca aagctttatc gtgttgtata aaaaaattaa caatataatg gcaataggta    4800
gagatacaac aaatgaatat aacactataa cacttcatat tttccaaatc ttaattggag    4860
tttaaggaag aaatcaataa atataaaata taagcacata tttattatat atctaaggta    4920
tacaaatctg tctacatgaa gtttacagat tggtaaatat cacctgctca acatgtaatt    4980
atttaataaa actttggaac attaaaaaaa taaattggag gcttaaaaaa aaaaaaaaaa    5040
a                                                                    5041
```

```
<210> SEQ ID NO 3
<211> LENGTH: 7
<212> TYPE: PRT
<213> ORGANISM: Homo sapiens

<400> SEQUENCE: 3

Lys Glu Pro Ala Pro Thr Thr
1               5
```